(12) United States Patent
Schmitt et al.

(10) Patent No.: US 10,119,923 B2
(45) Date of Patent: Nov. 6, 2018

(54) SYSTEMS AND METHODS FOR IMAGE RECONSTRUCTION AT HIGH COMPUTED TOMOGRAPHY PITCH

(71) Applicant: L3 Security & Detection Systems, Inc., Woburn, MA (US)

(72) Inventors: Michael Schmitt, Pinellas Park, FL (US); Andrew D. Foland, Wellesley, MA (US); Boris Oreper, Newton, MA (US)

(73) Assignee: L3 Security & Detection Systems, Inc., Woburn, MA (US)

( * ) Notice: Subject to any disclaimer, the term of this patent is extended or adjusted under 35 U.S.C. 154(b) by 93 days.

(21) Appl. No.: 14/886,883

(22) Filed: Oct. 19, 2015

(65) Prior Publication Data
US 2017/0108453 A1    Apr. 20, 2017

(51) Int. Cl.
*A61B 6/00* (2006.01)
*G01N 23/046* (2018.01)
*G06T 11/00* (2006.01)

(52) U.S. Cl.
CPC .......... *G01N 23/046* (2013.01); *G06T 11/006* (2013.01); *G01N 2223/401* (2013.01); *G01N 2223/408* (2013.01); *G01N 2223/419* (2013.01); *G01N 2223/643* (2013.01); *G06T 2211/424* (2013.01); *G06T 2211/436* (2013.01)

(58) Field of Classification Search
CPC .......... G01N 23/046; G01N 2223/401; G01N 2223/408; G01N 2223/419; G01N 2223/643; G06T 11/006; G06T 2211/424; G06T 2211/4362
See application file for complete search history.

(56) References Cited

U.S. PATENT DOCUMENTS

| | | | |
|---|---|---|---|
| 6,088,423 | A  | 7/2000  | Krug et al. |
| 7,362,847 | B2 | 4/2008  | Bijjani |
| 7,606,348 | B2 | 10/2009 | Foland et al. |
| 7,831,012 | B2 | 11/2010 | Foland et al. |
| 8,270,565 | B2 | 9/2012  | Oreper |
| 8,644,549 | B2 | 2/2014  | Foland et al. |
| 9,069,092 | B2 | 6/2015  | Oreper et al. |

(Continued)

FOREIGN PATENT DOCUMENTS

WO    2007004196 A2    1/2007

OTHER PUBLICATIONS

Crawford, Carl R., and Kevin F. King. "Computed tomography scanning with simultaneous patient translation." Medical physics 17.6 (Nov./Dec. 1990): 967-982.

(Continued)

*Primary Examiner* — Courtney Thomas
(74) *Attorney, Agent, or Firm* — McCarter & English, LLP; David R. Burns

(57) ABSTRACT

Methodologies, systems, apparatus, and non-transitory computer-readable media are described herein to facilitate acquisition of volumetric data and volumetric image reconstruction. An imaging system can be configured to transport an object at a speed relative to the scan path of an X-ray source such that insufficient measurement data is collected for classically complete geometrical coverage. Iterative image reconstruction techniques may be used to generate volumetric images based on measured volumetric data of at least a portion of the object.

46 Claims, 14 Drawing Sheets

(56) References Cited

U.S. PATENT DOCUMENTS

2010/0215144 A1* 8/2010 Basu .................. G01V 5/005
378/20
2014/0198899 A1 7/2014 Ziskin et al.

OTHER PUBLICATIONS

Danielsson, P. E., et al. "Towards exact 3D-reconstruction for helical cone-beam scanning of long objects: a new arrangement and a new completeness condition." International Meeting on Fully Three-Dimensional Image Reconstruction in Radiology and Nuclear Medicine (Nemacolin, PA). Jun. 25-28, 1997.

Feldkamp, L. A., L. C. Davis, and J. W. Kress. "Practical cone-beam algorithm." Journal of the Optical Society of America A 1.6 (Jun. 1984): 612-619.

International Search Report and Written Opinion of the International Searching Authority for International Application No. PCT/US2016/056853 dated Dec. 7, 2016.

Kachelrieß, Marc, Michael Knaup, and Willi A. Kalender. "Extended parallel backprojection for standard three-dimensional and phase-correlated four-dimensional axial and spiral cone-beam CT with arbitrary pitch, arbitrary cone-angle, and 100% dose usage." Medical Physics 31.6 (May 28, 2004): 1623-1641.

Katsevich, Alexander, Samit Basu, and Jiang Hsieh. "Exact filtered backprojection reconstruction for dynamic pitch helical cone beam computed tomography." Physics in Medicine and Biology 49.14 (Jun. 28, 2004): 3089.

Thibault et al. "A three-dimensional statistical approach to improved image quality for multislice helical CT." Medical physics 34.11 (Oct. 29, 2007): 4526-4544.

Wang, Ge, et al. "A general cone-beam reconstruction algorithm." IEEE Transactions on Medical Imaging 12.3 (Sep. 1993): 486-496.

Xue, Hui, et al. "An iterative reconstruction method for high-pitch helical luggage CT." Proc. SPIE 8506, Developments in X-Ray Tomography VIII, p. 85061O (Oct. 17, 2012).

Yan, Ming, and Cishen Zhang. "Tilted plane Feldkamp type reconstruction algorithm for spiral cone beam CT." Medical physics 32.11 (Oct. 25, 2005): 3455-3467.

Ye et al. "Minimum detection windows, PI-line existence and uniqueness for helical cone-beam scanning of variable pitch." Medical physics 31.3 (Feb. 18, 2004): 566-572.

Zou, Yu, et al. "PI-line-based image reconstruction in helical cone-beam computed tomography with a variable pitch." Medical physics 32.8 (Jul. 29, 2005): 2639-2648.

* cited by examiner

SYSTEMS AND METHODS FOR IMAGE RECONSTRUCTION AT HIGH COMPUTED TOMOGRAPHY PITCH

BACKGROUND

Imaging technologies incorporating penetrating radiation such as X-rays or gamma rays have found widespread use in applications as diverse as medical imaging and cargo inspection. X-ray imaging techniques involve aiming a beam of the radiation at an object to be imaged and measuring the intensity of X-rays received through the object. The attenuation of the X-ray beam depends on material properties of the object such as mass density or atomic species. By acquiring such attenuation data over a range of paths through the object, it is possible to reconstruct a three-dimensional or projected two-dimensional image of the object.

In security applications, the three-dimensional or projected two-dimensional images can be used to detect suspicious or dangerous objects hidden in baggage or cargo, for example, contraband.

SUMMARY

Taught herein are systems, methods and non-transitory computer readable media to detect suspicious or dangerous objects hidden in baggage or cargo. The systems, methods and non-transitory computer readable media taught herein provide an imaging modality that allows detection of suspicious or dangerous objects hidden in baggage or cargo even though there is insufficient measurement data to support classically complete geometrical coverage due to a high pitch scan parameter. A classically-complete source-detector geometry may be defined as one with complete pi-line coverage for a given speed of transport of an object that enables analytic inversion of projection measurements of the object.

In some embodiments taught herein, an imaging device is disclosed that includes a transport system, an X-ray source, a detector array, and a processing unit. The transport system transports an object into the imaging device and through an X-ray beam. The X-ray source emits a conical beam of X-ray radiation at a plurality of points along a trajectory of at least 180° about a direction of transport of the object to irradiate at least a portion of the object. The detector array detects measurement data indicative of an interaction of the X-ray radiation with at least the portion of the object. The detector array is disposed relative to the X-ray source to detect the measurement data along a scan path about the object. The processing unit has a central processing unit programmable to operate the imaging device in one of a first mode or a second mode. In the first mode, a speed of the transport system relative to the scan path is controlled to cause the detector array to detect measurement data that is sufficient for complete pi-line coverage. In the second mode, the speed of the transport system relative to the scan path is controlled to cause the detector array to detect measurement data that is insufficient for complete pi-line coverage. The central processing unit is also programmable to compute reconstructed volumetric data representative of a volume of the object in the first mode or the second mode by applying at least one iteration of an iterative reconstruction to the measurement data to derive the reconstructed volumetric data.

As taught herein, in some embodiments an imaging system is disclosed that includes a transport system, an X-ray source, a detector array, and a processing unit. The transport system includes a conveyor to transport an object into the imaging system. The X-ray source is configured to emit a conical beam of x-ray radiation at a plurality of points along a trajectory of at least 180° around the conveyor on a scan path relative to a direction of transport of the object, to irradiate at least a portion of the object. The detector array detects measurement data indicative of an interaction of the x-ray radiation with the portion of the object, and the detector array is disposed relative to the X-ray source to detect the measurement data along the scan path. The processing unit has a central processing unit programmable to instruct the transport system to transport the object at a speed relative to the scan path to cause the detector array to detect measurement data that is insufficient for complete pi-line coverage due to a speed of traversal of the object relative to the scan path of the conical beam. The central processing unit is also programmable to compute reconstructed volumetric data representative of a volume of the object by applying at least one iteration of an iterative reconstruction to the measurement data to derive the reconstructed volumetric data.

As taught herein, in some embodiments a method for reconstructing an image of a volume of an object from a cone-beam radiation pattern is disclosed. Performance of the method receives measurement data indicative of an interaction of X-ray radiation from a conical beam with at least a portion of an object disposed in a scan path thereof. The measurement data is insufficient for complete pi-line coverage due to a speed of traversal of the object relative to the scan path of the conical beam. Performance of the method computes, using at least one processing unit having a central processing unit, reconstructed volumetric data representative of a volume of the object by applying at least one iteration of an iterative reconstruction methodology to the measurement data to derive the reconstructed volumetric data. Further, performance of the method computes, using the at least one processing unit, a volumetric image of the volume of the object based on the reconstructed volumetric data.

In some embodiments taught herein, an image reconstruction module for an imaging device is disclosed. The image reconstruction module includes a communication interface, a memory, and a programmable processing unit. The memory stores processor-executable instructions for an iterative reconstruction methodology for computing reconstructed volumetric data representative of a volume of an object. The programmable processing unit has a central processing unit, communicatively coupled to the communication interface and the memory. Execution of the processor-executable instructions allows the programmable processing unit to have several operations. The programmable processing unit operates to receive measurement data indicative of an interaction of X-ray radiation from a cone-beam radiation pattern with at least a portion of an object disposed in a scan path thereof. The measurement data is insufficient for complete pi-line coverage due to a speed of traversal of the object relative to the scan path. The programmable processing unit operates to compute reconstructed volumetric data representative of a volume of the object by applying at least one iteration of an iterative reconstruction methodology to the measurement data to derive the reconstructed volumetric data. The programmable processing unit operates to compute a volumetric image of the volume of the object based on the reconstructed volumetric data. The programmable processing unit operates to control the communication interface to transmit, or control the memory so as to store, the volumetric image or the reconstructed volumetric data.

Disclosed herein are in some embodiments one or more non-transitory machine readable media storing instructions executable by a processing device having a central processing unit. Execution of the instructions causes the processing device to carry out a methodology for reconstructing a volume of an object from a cone-beam radiation pattern. The medium includes instructions to receive measurement data indicative of an interaction of X-ray radiation from a cone-beam radiation pattern with at least a portion of an object disposed in a scan path thereof. The measurement data is insufficient for complete pi-line coverage due to a speed of traversal of the object relative to the scan path. The medium includes instructions to compute reconstructed volumetric data representative of a volume of the object by applying at least one iteration of an iterative reconstruction methodology to the measurement data to derive the reconstructed volumetric data. The medium includes instructions to compute a volumetric image of the volume of the object based on the reconstructed volumetric data.

BRIEF DESCRIPTION OF THE DRAWINGS

The skilled artisan will understand that the drawings are primarily for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar or structurally similar elements).

The foregoing and other features and advantages provided by the present disclosure will be more fully understood from the following description of exemplary embodiments when read together with the accompanying drawings, in which.

DETAILED DESCRIPTION

Figure 1:
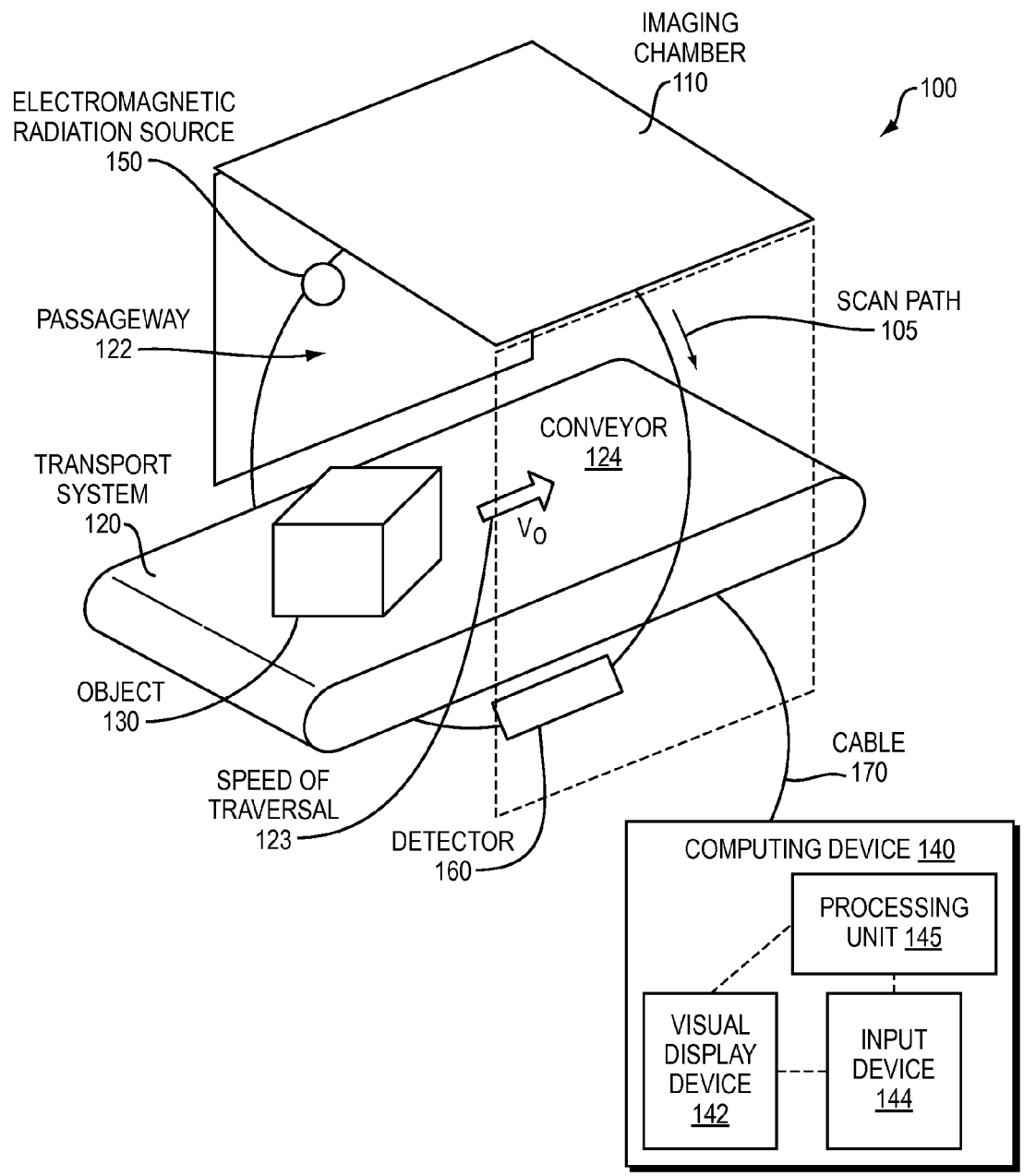
FIG. 1 illustrates an example imaging system, according to embodiments of the present disclosure.

Systems, methodologies, computer readable media, and apparatuses of the present disclosure enable volumetric image reconstruction by computed tomography systems to identify contraband, explosives, or other chemical or material components within objects. In particular, volumetric image reconstruction is taught for situations when the object being imaged is traveling at speeds such that the measured data collected by radiation detectors is insufficient for complete pi-line coverage. An imaging system is disclosed that can transport an object past an X-ray radiation source and a radiation detector. The speed of transport can be controlled such that the detected measurement data is insufficient for classically complete geometrical coverage. Methodologies are taught to enable volumetric image reconstruction, and computer readable media are disclosed containing instructions to implement volumetric image reconstruction from such measurement data. The disclosed systems, methodologies, computer readable media, and apparatuses of the present application advantageously enable faster scanning of objects as well as providing a user with the ability to change the speed of object transport to suit the requirements of an application.

Below are more detailed descriptions of various concepts related to, and examples of, methodologies, computer readable media, apparatuses, and systems for volumetric image reconstruction, particularly at high computed tomography (CT) pitch. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "classically-complete" refers to a source-detector geometry that provides complete pi-line coverage (or band-limited coverage in some examples) at a given speed of transport of an object, enabling analytic inversion of the projection measurements. An example discussion of classically-complete geometry is provided in, for example, Y. Ye et al., "Minimum detection windows, PI-line existence and uniqueness for helical cone-beam scanning of variable pitch." Medical physics 31.3 (2004): 566-572. Pi-line coverage that is complete at a given transport speed may fail to be complete at higher values of transport speed. It is readily apparent to one of ordinary skill in the art that a given point in space within the classically complete field of view of a detector, such as but not limited to a scanner, may or may not be classically-complete at higher transport speeds, depending on the phase of the source-detector geometry. For example, some points of the object that fall near the periphery of the field of view may or may not receive classically-complete coverage depending upon the phase of the source-detector geometry. In an example, the phase of the source-detector geometry can be modified by changing (e.g., increasing) the speed of the x-ray source. Such a change also affects the range of speed of transport of the object that can be used to achieve pi-line coverage. Based on the disclosure herein, it will be readily apparent to one of ordinary skill in the art that the term "classically-complete" geometries can encompass analytical, continuous pi-line coverage as well as discretized pi-line coverage that may include some edge effects.

As used herein, the term "pitch" refers to the advance of an object per X-ray source rotation divided by detector height along the dimension of object travel, relative to the advance for which complete geometrical coverage is obtained. As defined herein, a value of pitch of 1 indicates that an object is moving at the highest speed at which measured data is sufficient for complete pi-line coverage based on the relative arrangement of the sensor(s) and detector(s), holding the other machine parameters substantially constant.

As used herein, the term "high CT pitch" encompasses values of pitch greater than 1 where the value of pitch indicates that the measured data is insufficient for complete pi-line coverage. Acceptable images can be obtained from measurement data collected at values of pitch as high as about 2. For some example implementations, acceptable image quality can be obtained from measurement data collected for pitches even higher than 2. There may be no intrinsic limitation on the value of pitch beyond which image reconstruction of some quality can be obtained according to the principles herein.

As used herein, the term "insufficient for complete pi-line coverage" encompasses the concepts of "incomplete pi-line coverage" or "pi-line incompleteness" and indicates that the measurement data does not contiguously map out the full 180° arc corresponding to a complete pi-line relative to the detection plane. As a non-limiting example, the term "insufficient for pi-line coverage" could correspond to data that maps out only about 95%, about 90%, about 80%, about 75% or less of the arc corresponding to the pi-line.

In addition to the analytic geometrical specifications described herein for reconstruction of arbitrary continuous functions, there can be additional requirements associated with obtaining discretely organized data (e.g., at discrete detectors or discrete sampling times). Example sampling theorems such as those associated with Nyquist and Candes put band-limits or other limits (i.e., restricted isometry) on the kinds of arbitrary functions that can be reconstructed with arbitrary accuracy using a given sampling scheme. A sampling scheme which does not satisfy these additional requirements at the spatial reconstruction frequency under consideration also may be defined as classically incomplete.

Example methodologies, systems, apparatus, and non-transitory computer-readable media are described herein to facilitate acquisition of volumetric data and volumetric image reconstruction in security and detection system environments. Some embodiments involve imaging systems that transport an object at a speed relative to the scan path of an X-ray source that results in the collection of insufficient measurement data for complete pi-line coverage. In other words, the speed of the object relative to the scan path of an X-ray beam does not allow collection of sufficient measurement data to satisfy a pi-line reconstruction requirement.

FIG. 1 illustrates an exemplary imaging system 100 for generating a reconstructed image of at least a portion of an object 130, according to one embodiment of the present disclosure. The imaging system 100 includes a scanner 110, a transport system 120 to transport an object 130, a computing device 140, an X-ray source 150, and a detector 160. The scanner encloses a tunnel 122. The computing device 140 can include an input device 144 and a processing unit 145 and can render an image and other interfaces on a visual display device 142.

The transport system 120 can be configured to transport the object 130 through at least a portion of the tunnel 122 of the scanner 110. In accordance with various embodiments, the transport system 120 can include an object transport mechanism such as, but not limited to, a conveyor belt 124, a series of rollers, or a cable that can couple to and pull an object 130 into the scanner 110. The transport system 120 can be configured to transfer the object 130 into the tunnel 122 of the scanner 110 at a range of speeds. For example, the transport system 120 may operate to transport the object 130 at speeds between about 5.0 cm/s and about 40 cm/s, slower than about 5.0 cm/s, or faster than about 40 cm/s. In some embodiments, the transport system 120 can operate to transport the object 130 at speeds up to about 75 cm/s. Although some examples herein are described relative to specific values of speed of transport, it should be understood that there is no limitation on speed of transport applicable to the embodiments described herein.

The transport system 120 may transfer an object 130 at more than one speed and may also stop or move in reverse. In some embodiments, the speed of traversal 123 of the transport system 120 can be used to determine the most appropriate methodology to apply for volumetric data reconstruction. As will be described in greater detail below, the speed of the transport system 120 can be varied by the computing device 140 or by use of a manual switch or dial. The transport system 120 can contain a controller with a central processing unit (for example, a microcontroller) that is able to receive instruction from the computing device 140 and adjust or maintain a speed of the transport system 120 in accordance with said instructions. The imaging system 100 and the transport system 120 can transport the object 130 at a speed of traversal ($v_0$) 123 relative to the scan path 105 of the conical beam of the X-ray source 150 to obtain incomplete pi-line coverage of an object 130. Systems, methodologies, computer readable media, and apparatuses taught herein can be used to apply at least one iteration of an iterative reconstruction to such measurement data indicative of insufficient pi-line coverage to derive reconstructed volumetric data or reconstructed images of portions of the object 130.

As will be discussed in more detail below, an example system can be configured to perform scanning in two different modes based on the speed of transport of the object. As a non-limiting example, in risk-based screening, baggage may be reviewed differently at two levels of risk. For example, as taught herein, a system may be configured to have a first "complete geometry" mode at a relatively lower speed to provide more detailed, artifact-free images for higher-risk baggage or other containers and a second "high-throughput" mode at substantially higher speed for lower-risk or other containers. In this example, the source-detector trajectories can be configured to provide the low-speed mode with classically complete geometrical coverage in the first mode, and geometrical coverage that may be expected to be incomplete due to the speed of traversal in the second mode. The images obtained from applying direct reconstruction to measurement data collected in the second, high-throughput mode of operation may be at lower resolution. The high-throughput mode also may include imaging considerations that are acceptable for lower-risk bags such as image artifacts or additional processing, or can utilize different image reconstruction algorithms and/or threat detection algorithms and associated methods. As taught herein, the second, high-throughput mode of this example system can be implemented with the lesser hardware demands characteristic of the first, lower-speed mode and can result in a device with reduced cost and complexity.

Accordingly, in an example implementation, imaging system 100 and the transport system 120 can transport the object 130 at two or more different speeds of traversal 123 relative to a scan path 105 of the conical beam of the X-ray source 150. At least one of the speeds of traversal causes the imaging system 100 to obtain measurement data indicative of complete pi-line coverage of an object 130, and at least one other speed of the two or more different speeds causes the imaging system 100 to obtain measurement data indicative of insufficient pi-line coverage. The ability to operate an imaging device 100 in two or more modes having different speeds of traversal 123 using the transport system 120 is advantageous because the speed can be adjusted to meet situational needs as discussed hereinabove. Other benefits of the example imaging systems herein include the capability of increasing the speed of traversal 123 when the size of a queue of objects to be scanned increases past a certain level, while still obtaining acceptable reconstruction images of the objects. Conversely, the speed of traversal 123 may be decreased if directed by security authorities or in response to a change in, for example, national security threat level. In some embodiments, to derive the two or more different modes of operation, the imaging system 100 may be operated at two or more different speeds of traversal 123 of the object 130 via the transport system 120, while the phase of the source-detector geometry is held constant. In other embodiments, to derive the two or more different modes of operation, the speed of traversal 123 of the object 130 via the transport system 120 may be kept the same, while the phase of the source-detector geometry is changed for each different mode. For example, the phase of the source-detector geometry can be changed by moving the X-ray source 150 at different speeds along the scan path 105.

The X-ray source 150 can be configured to emit a conical beam of X-ray radiation (or gamma rays, or other radiation) at a plurality of points along a trajectory of at least 180° around the conveyor 124 on a scan path 105 relative to a direction of transport of the object 130, to irradiate at least a portion of the object 130. In some embodiments, the source 150 can emit gamma rays. The detector 160 can be configured to detect measurement data indicative of an interaction of the X-ray radiation with the portion of the object 130. The detector 160 is disposed relative to the X-ray source 150 to detect the measurement data along the scan path 105. The relationship and operation of the X-ray source 150 and the detector 160 are discussed below in more detail. In some embodiments, the source 150 and detector 160 can have a fixed spatial relationship and may rotate about a longitudinal axis of the imaging system 100 as, for example, on a gantry. Embodiments containing a source 150 and detector 160 attached to a gantry are described in greater detail below with reference to FIG. 2.

The computing device 140 can include at least one processing unit 145 including at least one central processing unit (CPU). The processing unit 145 is programmable to execute processor-executable instructions to instruct the transport system 120 to transport the object 130 at a speed of traversal 123 relative to the scan path 105 to cause the detector 160 to detect measurement data that is insufficient for complete pi-line coverage due to a speed of traversal 123 of the object 130 relative to the scan path 105 of the conical beam. The combination of the speed of traversal of the object 130 and the angular speed of revolution of the source 150 along the scan path 105 can produce a helical scan path having a pitch greater than one. Due to this high value of pitch, less than 180° of coverage is provided for any point in an object 130. Nevertheless, as disclosed herein, image reconstruction can be performed as discussed in more detail below.

The central processing unit is programmable to compute reconstructed volumetric data representative of a volume of the object 130 by applying at least one iteration of an iterative reconstruction to the measurement data to derive the reconstructed volumetric data. The computing device 140 and the processing unit 145 are discussed in greater detail with respect to FIG. 11.

The computing device 140 including the processing unit 145 can be configured to exchange data, or instructions, or both data and instructions, with at least one of the other components of the imaging system 100 wirelessly or via one or more wires or cables 170. The computing device 140 and, for example, the transport system 120 can digitally communicate to send or receive data or instructions or both. For example, the computing device 140 can transmit instructions to a controller of the transport system 120 to cause the transport of the object 130 to speed up, slow down, or maintain a speed of traversal ($v_o$) 123 relative to a scan path 105 of a conical beam of an X-ray source 150. As another example, the computing device 140 including the processing unit 145 can communicate with the X-ray source 150 or the detector 160 to control the operation of each and receive measurement data from the detector 160. The computing device 140 including the processing unit 145 can receive measurement data that is representative of a volume of the object 130 and can be configured or programmed to apply at least one iteration of an iterative reconstruction to the measurement data to derive the reconstructed volumetric data.

As shown in FIG. 1 and described further below with respect to FIG. 11, the computing device 140 can include a visual display device 142, an input device 144, and the processing unit 145. Output from the detectors 160 can be processed by the processing unit 145 to produce measurement data corresponding to volume information of the object 130. The visual display device 142 can be configured to allow a user to view a reconstructed image of the object 130. The computing device 140 can render a user interface on the visual display device 142 to allow an operator of the imaging system 100 to interact with the user interface with an input device 144. In one embodiment, the user interface is a graphical user interface. The input device 144 can be a keyboard, a mouse, a trackball, a touchpad, a stylus, a touchscreen of the visual display device 142 or any other suitable device that allows a user to interface with the computing device. In some embodiments, a graphical user interface (GUI) can be rendered on a touchscreen to allow a user to input information or data.

The scanner 110 may be made of appropriate metal or plastic materials that allow the desired spacing and orientation of the X-ray source 150 and the detector 160 relative to the object 130. In some embodiments, the scanner 110 may include radiation stopping or absorbing material such as lead.

The object 130 to be imaged can enter the scanner 110 through the tunnel 122. The size of the tunnel 122 may be of any shape that meets application-specific requirements. For example, the tunnel 122 may be configured with a passageway sized to allow the transport of hand-carry luggage, checked luggage, cargo, shipping containers, or any other type of object. The tunnel 122 may be configured with any geometric conformation. As non-limiting examples, the tunnel 122 can have a circular cross-section, a square cross-section, a rectangular cross-section, a hexagonal cross-section, an oval cross-section, or other polygonal-shaped cross-section. In another example, tunnel 122 can have an irregularly-shaped cross-section.

The scanner 110 can house one or more X-ray sources 150 and detectors 160. In accordance with various embodiments, the X-ray source 150 may be an X-ray source or a gamma ray source. The X-ray source(s) 150 can be configured to emit a cone-beam of radiation to interact with the object 130, and the detectors 160 can be configured to detect radiation indicative of an interaction of the radiation with any portion of the object. As a non-limiting example, the detector 160 can detect attenuated radiation that has passed through a portion of the object 130. In some embodiments, the X-ray source 150 and detector 160 can move cooperatively along a scan path that may be defined relative to the motion of an object 130. For example, the scan path may be a partial or complete circle of constant radius where the object 130 travels along a line passing through a central portion of the circle. As described in greater detail below with reference to FIG. 8, the X-ray source 150 of some embodiments can include a high-energy electron beam and an extended target or array of targets. In some embodiments, imaging systems as taught herein can have more than one source and detector and are described in greater detail below with reference to FIG. 9.

In some embodiments, the detector 160 may be configured as an array of multiple detectors.

The processing unit 145 can be configured to generate volumetric data from the radiation detected by the detectors 160 using any suitable image reconstruction methodology. Examples of direct reconstruction techniques that may be used to reconstruct volumetric data in some embodiments include filtered back-projection methodology, an analytical cone-beam methodology, an approximate cone-beam methodology, a Fourier reconstruction methodology, an extended parallel back-projection methodology, a filtered back-projection with dynamic pitch methodology, a pi-line-based image reconstruction methodology, a Feldkamp-type reconstruction methodology, a tilted-plane Feldkamp-type reconstruction methodology, or any other direct reconstruction technique that meets application-specific requirements.

Iterative reconstruction techniques may also be employed in the system 100 to reconstruct volumetric data. Examples of iterative reconstruction techniques include a simultaneous algebraic reconstruction technique (SART), a simultaneous iterative reconstruction technique (SIRT), an ordered subset convex technique (OSC), ordered subset maximum likelihood methodologies, an ordered subset expectation maximization (OSEM) methodology, an adaptive statistical iterative reconstruction technique (ASIR) methodology, a least squares QR methodology, an expectation maximization (EM) methodology, an OS-separable paraboloidal surrogates technique (OS-SPS), an algebraic reconstruction technique (ART), a Kacsmarz reconstruction technique, or any other iterative reconstruction technique or methodology that meets application-specific requirements. In some embodiments, a sparse matrix or a compressed sensing technique can be used to increase the speed of the reconstruction.

Iterative reconstruction techniques require that an initial state be defined before successive iterative steps can be performed. When initialized using an empty or uniform set, an iterative reconstruction technique may often perform many iterations before achieving convergence. Each iteration step is computationally intensive, so conducting many iteration steps can unacceptably increase the total time for data reconstruction. In accordance with various embodiments, the process of iterative reconstruction can be initialized using the output from a direct reconstruction technique including, but not limited to, a filtered back-projection methodology. The use of output from a direct reconstruction technique can significantly reduce the number of iterations to reach convergence and speed up total processing time.

In accordance with various embodiments, measurements obtained from a detector 160 may be used by the processing unit 145 to reconstruct a three-dimensional (i.e., volumetric) representation of properties of the object 130 or to produce two-dimensional projections of properties of the volume of the object 130 along slices. In various embodiments, measurement data or reconstructed images or representations may be stored and retrieved for analysis at a later date or may be displayed to a user on the visual display device 142. A slice of the object 130 can be defined as a two-dimensional array of data where each element of the array has the same value of the longitudinal coordinate (i.e., the coordinate along the direction of transport of the object). In some embodiments, the orientation of the slice can be defined by the plane in which the scan path 105 lies. The slices may be oriented perpendicular to the direction of motion or along any other dimensions as may be required. The volumetric image can represent one or more properties of the object 130 being imaged, which may be under inspection to identify contraband. For example, the radiation emitted by the X-ray source 150 may attenuate as it passes through a portion of the object 130 before impinging on a detector 150. This attenuation is proportional to the density of the portion of the object 130 through which it traveled. Accordingly, the volumetric image can represent information about the density of the portion of the object. In another embodiment, radiation at two different energy levels may be directed such that they pass through a portion of the object 130. The ratio of the attenuation between beams at two different energy levels can provide information about the atomic number or elemental composition of the portion of the object 130. The system 100 according to the principles taught herein may be configured to compute volumetric data corresponding to the density, or atomic number, or both density and atomic number properties, of a portion of the volume of object 130.

Figure 2:
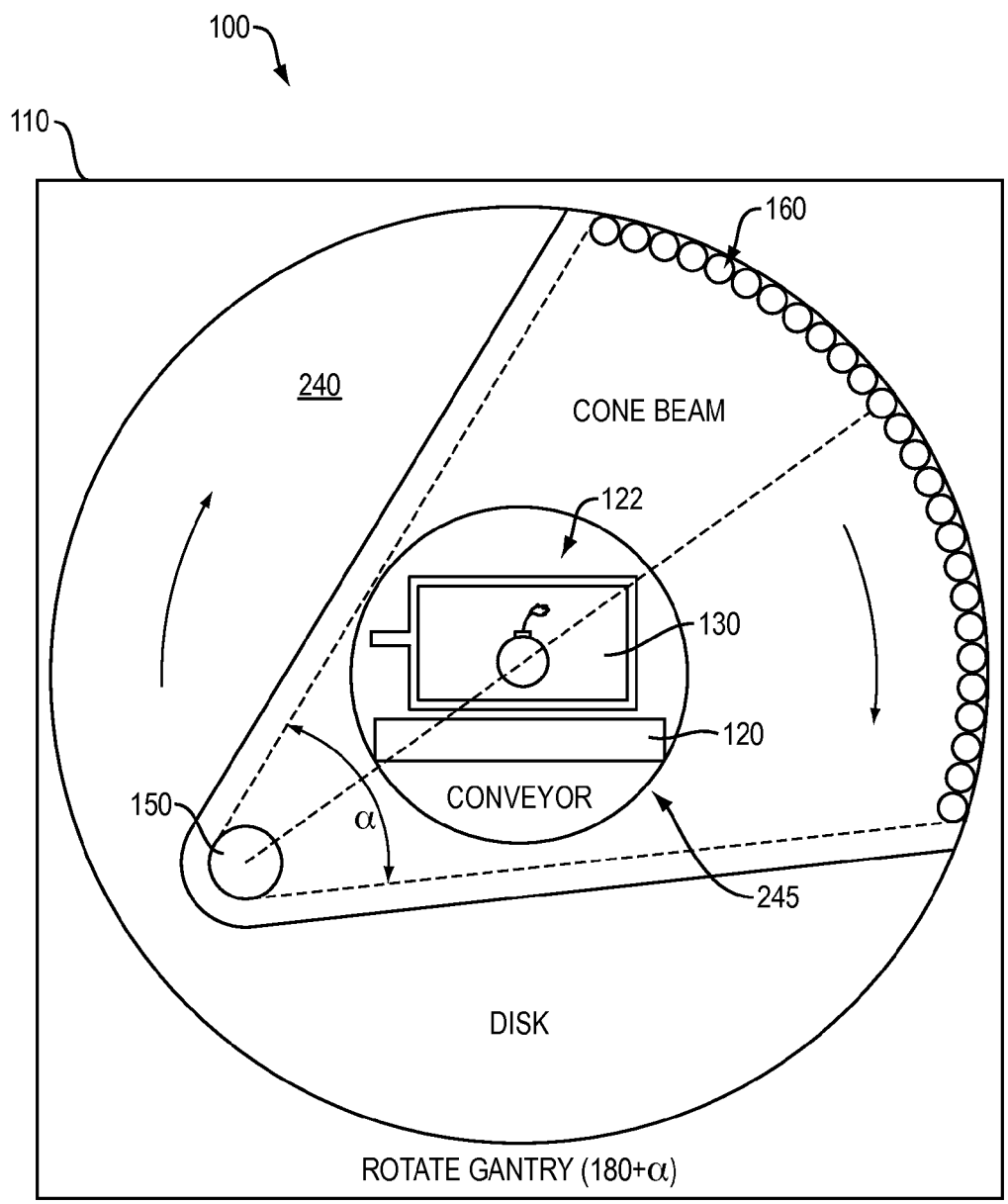
FIG. 2 illustrates an end view of an example imaging device including a rotating gantry, according to embodiments of the present disclosure.

FIG. 2 illustrates a cross-sectional view of the imaging system 100 including a rotating gantry 240 according to various embodiments taught herein. The gantry 240 can be located between the tunnel 122 and the wall of the scanner 110. The X-ray source 150 and detector 160 can be coupled to the gantry 240, which may rotate about a longitudinal axis defined by the direction of transport of the object 130. The inner bore 245 of the gantry 240 is large enough to pass the object 130 and the conveyor 120 therethrough. The gantry 240 can rotate around the path of the transported object 130 to enable observation of the object 130 from multiple angles along a helical scan path. In various embodiments, the gantry 240 can rotate through an angle of at least about 180°, at least about 180°+a (where a is the beam spread width of the X-ray source 150), or up to about 360° around the path of the transported object 130. In certain embodiments, the gantry can rotate at between about 90 RPM and about 300 RPM.

Figure 3A:
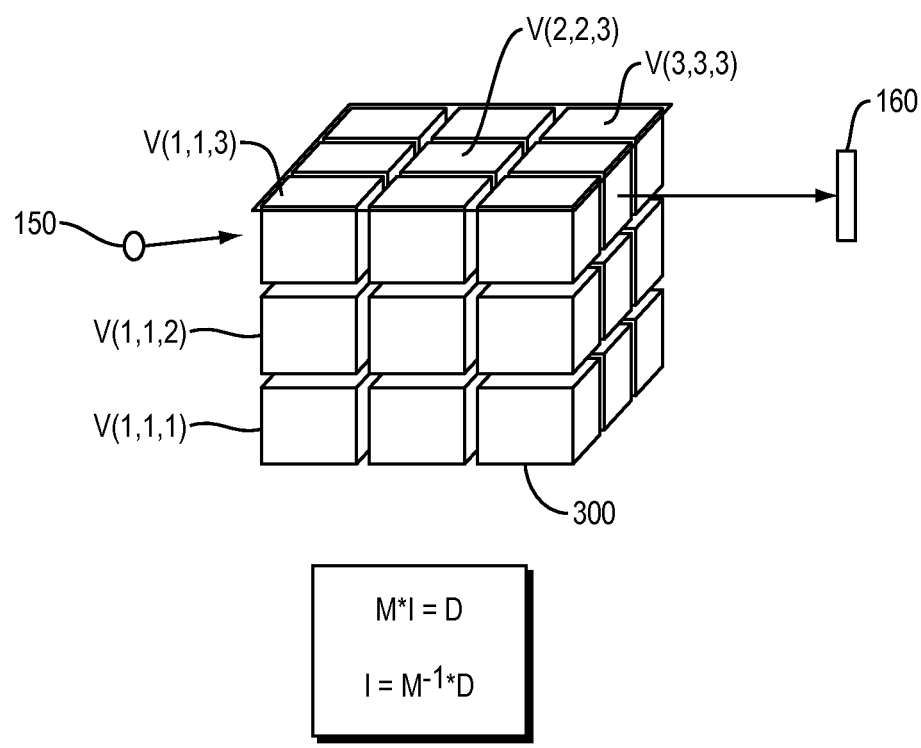
FIGS. 3A and 3B illustrate example representations of reconstruction geometries, according to embodiments of the present disclosure.

FIG. 3A illustrates a three-dimensional representation of the object 130 as an array of voxels 300. The object 130 is represented in FIG. 3A by twenty-seven voxels 300 whereas an object 130 in an actual reconstruction would be represented by a much larger number of voxels 300. In FIG. 3A, several voxels are numbered (i.e., V(1,1,1), V(1,1,2), V(1, 1,3), V(2,2,3), and V(3,3,3)). Rays emanate from an X-ray source 150 and pass through some voxels 300 representing the object 130 before striking a detector 160. In the present disclosure, image reconstruction is used to compute a volumetric data set including values of a material property such as mass density or atomic number for each of the voxels based on the measurement outputs from detectors. In some embodiments, the reconstruction can be used to determine an average value of one or more material properties within each voxel. For example, the average material property can be density, atomic number, or both density and atomic number.

Figure 3B:
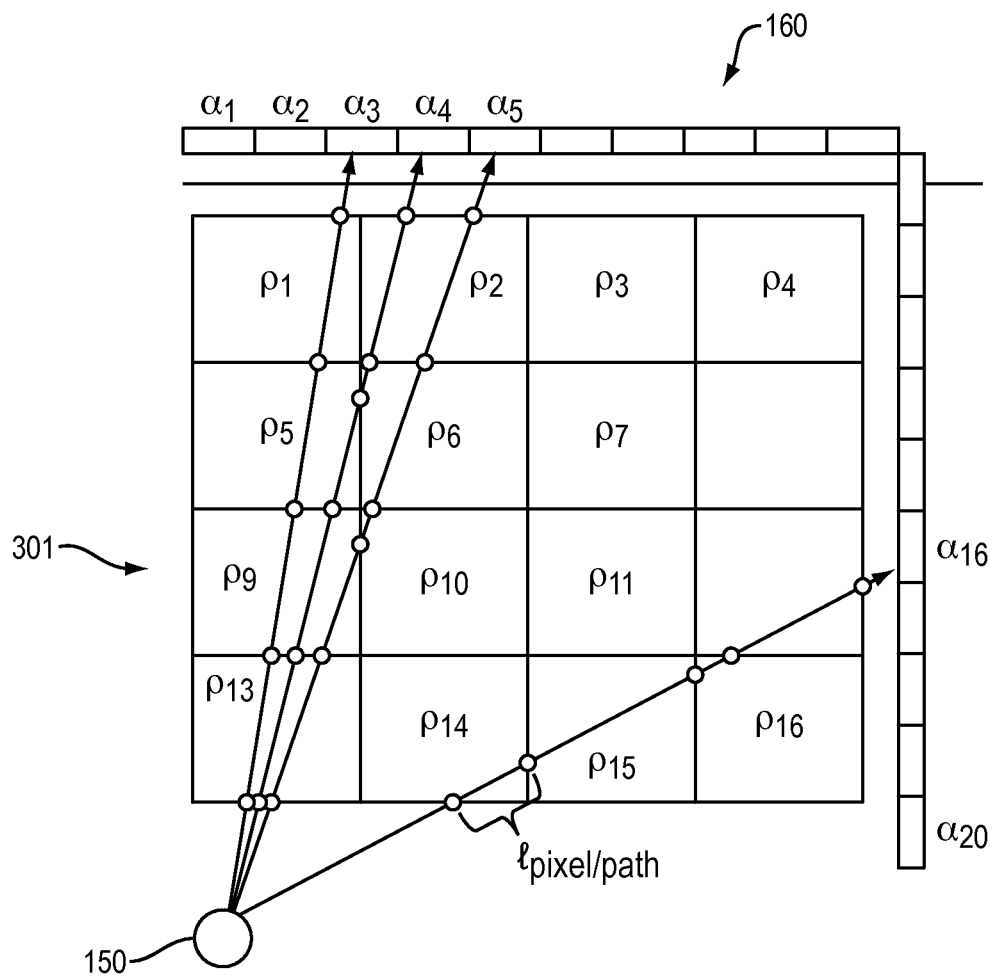

FIG. 3B illustrates a two-dimensional representation of an image slice of the object 130 as an array of pixels 301. The object 130 is represented in FIG. 3B by sixteen pixels 301 to facilitate explanation. Those skilled in the art will appreciate that each representational slice of the object 130 in an actual reconstruction would be represented by a much larger number of pixels 301, for example, one million pixels. The pixels are numbered as $\rho_1$-$\rho_{16}$. Rays emanate from an X-ray source 150 and pass through at least some of the pixels 301 representing the object 130 before striking a detector or array of detectors 160. In FIG. 3B, each of the positions from $\alpha_1$-$\alpha_{20}$ may represent a single detector in a detector array 160 or may represent sequential positions of a single detector as it moves around an object 130. In the present disclosure, image reconstruction is used to compute a volumetric data set including values of a material property such as mass density or atomic number for each of the pixels based on the measurement outputs from detectors. In some embodiments, the reconstruction can be used to determine an average value of one or more material properties within each pixel. For example, the average material property can be density, atomic number, or both density and atomic number.

In some embodiments, measurements are made by detecting penetrating radiation after it has passed from the X-ray source through an object 130. In the representational example shown in FIG. 3B, the radiation may be depicted as a ray connecting the X-ray source 150 and one or more locations of detector(s) 160. A comparison between the measured intensity when the object 130 is present and the expected intensity without an object 130 present produces an attenuation value corresponding to the path taken by that ray. A proportionate weight can be assigned to each pixel along the ray's path equal to the length of the line within the pixel to the total length of the ray path. When the attenuation values for a sufficient number of rays at a sufficient number of angles are obtained, the attenuation data can be processed to compute a material property for each pixel.

For example, FIG. 3B illustrates an X-ray source 150 and several positions of a detector 160. A ray traveling from X-ray source 150 to a detector at position $\alpha_5$ passes through pixels $\rho_2$, $\rho_6$, $\rho_9$, $\rho_{10}$ and $\rho_{12}$. As a result, the value detected by a detector at location $\alpha_5$ will depend on the material properties in each of those pixels. Thus, the measurement taken by a detector at $\alpha_5$ of a ray from X-ray source 150 may be used as part of an estimate of material properties such as density or atomic number at each of the pixels $\rho_2$, $\rho_6$, $\rho_9$, $\rho_{10}$ and $\rho_{12}$.

The measured outputs of the detectors may be used to define a system of simultaneous equations that, using an iterative mathematical technique, may be solved for the unknown values representing the material property of the individual pixels 301 in a slice of the object 130. Because variations in the measurement process may prevent a single solution from satisfying simultaneously all equations in a system of simultaneous equations, solving the system of equations formed from actual measurements would involve iteratively seeking the values that best solve the equations. Similarly, obtaining measurements from multiple angles allows material properties in each of the pixels 300 representing a slice of the object 130 to be computed using a direct method.

Those skilled in the art will appreciate that the pixels described above with reference to FIG. 3B are meant to facilitate explanation of embodiments taught herein. In a reconstruction as taught herein, the object 130 is represented by voxels (i.e., volume pixels) rather than by pixels, and the line paths of the rays can travel through the object along three dimensions rather than solely within a single slice of the object 130. An example of a voxel is illustrated above in FIG. 3A and below in FIG. 4.

Figure 4:
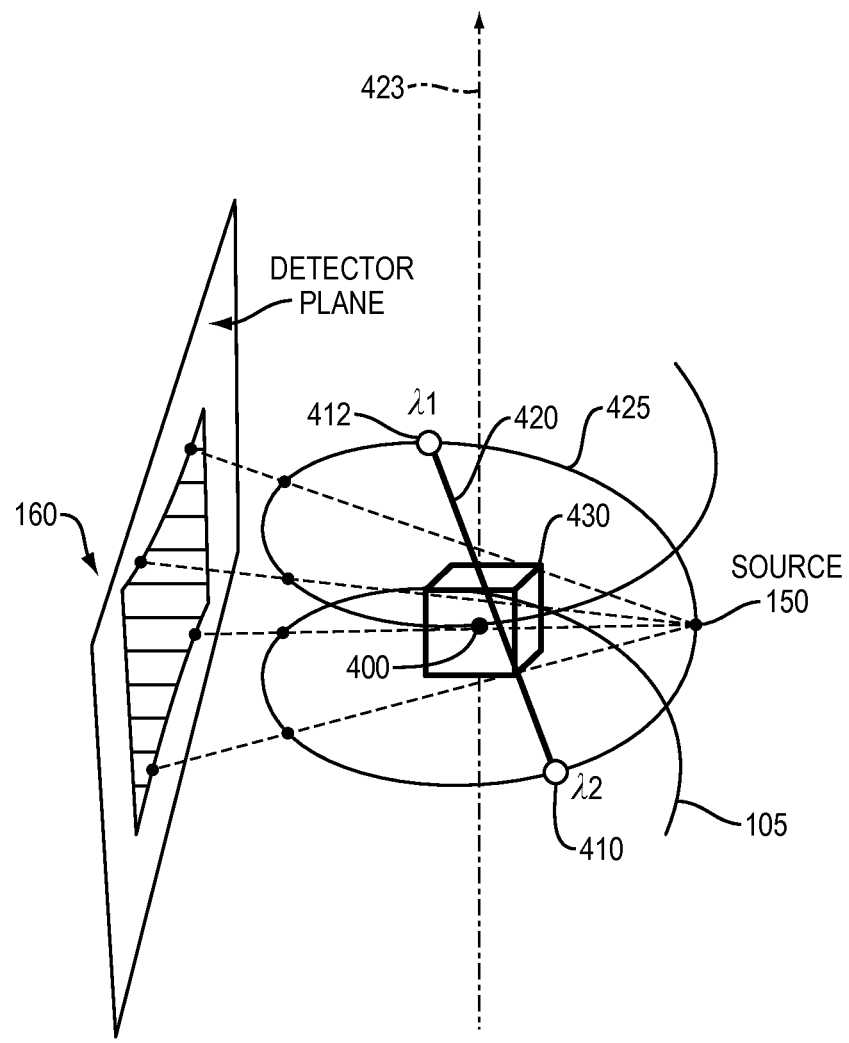
FIG. 4 illustrates an example of a pi-line relative to a detection plane, according to embodiments of the present disclosure.

FIG. 4 illustrates an example imaging geometry according to some embodiments taught herein. The imaging geometry is taken from the frame of reference of an arbitrary point 400 within the object 130. In the imaging device 100, for example, the object 130 moves longitudinally relative to the radial motion of the source 150 and the detector 160. To visualize the concept of a pi-line, it is helpful to explain the object 130 as motionless and have the source 150 and detector 160 move relative to the object 130. In this frame of reference (shown in FIG. 4), the point 400 within the object 130 is unmoving while the X-ray source 150 and detector 160 rotate around the point and advance forward in a direction 423 along a scan path 105. In imaging system 100, the helical nature of the scan path 105 is a result of the object 130 moving longitudinally while the source and detector rotate about an axis of rotation in a radial plane.

At a point $\lambda_2$ 410, the cone-beam of the X-ray source 150 first begins to illuminate the arbitrary point 400. As the X-ray source 150 advances forward along the scan path 105 in the frame of reference of this example, the arbitrary point 400 continues to be illuminated from different angles. Finally, the cone-beam reaches a point $\lambda_1$ 412 located 180° away from point $\lambda_2$ 410. The scan path traveled by the X-ray source 150 and detector 160 in the frame of reference of this example is known as the pi-segment 425 because the scan path traverses 180° or it radians. The shortest line connecting points $\lambda_2$ 410 and $\lambda_1$ 412 is known as the pi-line 420. Thus, a complete pi-line 420 indicates that information has been obtained for a point in the object 130 from a complete set of angles over 180°. Conversely, an incomplete pi-line 420 indicates that information has been obtained for each point in the object 130 from less than the complete set of angles over 180°.

Although the X-ray source 150 and detector 160 are depicted as traveling along a helical scan path 105 in the frame of reference of FIG. 4, it will be understood that the scan path 105 may in fact be a connected path of any shape such as a straight line or may include disconnected or disjointed segments. Further, the X-ray source 150 and detector 160 may be physically rotating as in the embodiments described with respect to FIG. 2 or may be stationary as described further below with reference to FIGS. 8 and 9. Non-helical paths are representative of geometries in which the source or detector are fixed in space.

Figure 5A:
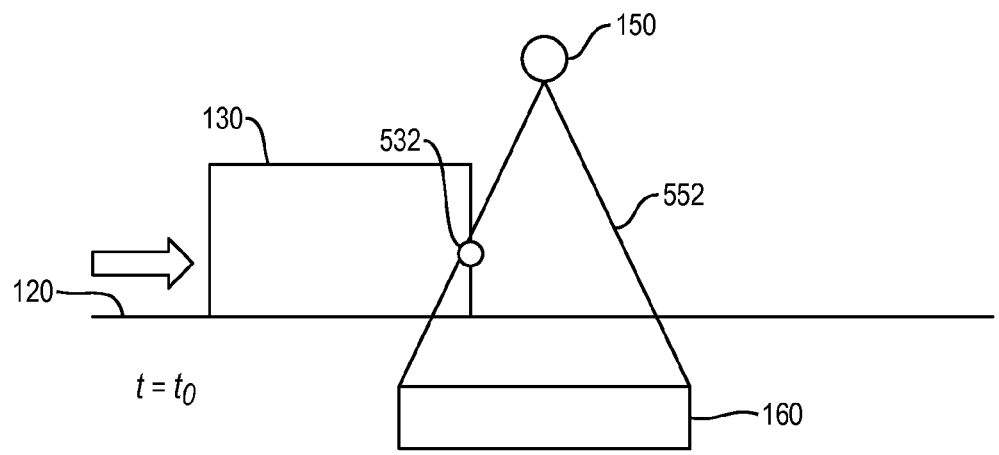
FIGS. 5A-5C illustrate examples of angular imaging coverage for different values of pitch, according to embodiments of the present disclosure.
Figure 5B:
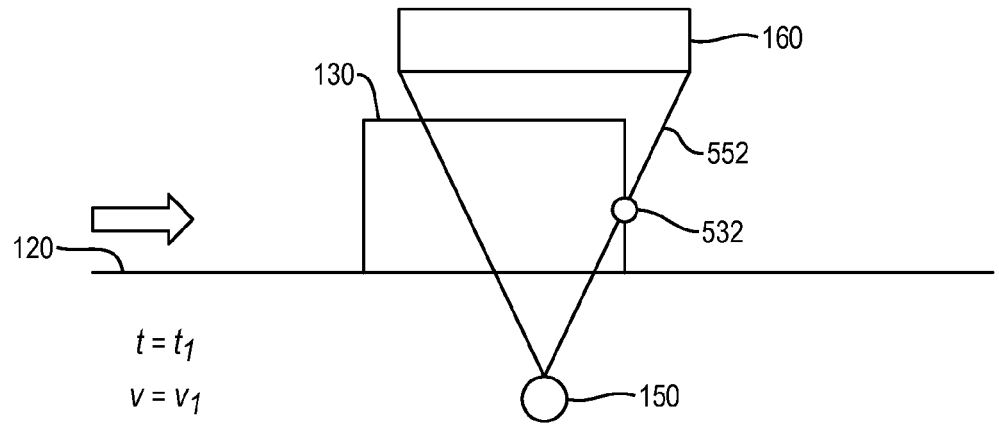
Figure 5C:
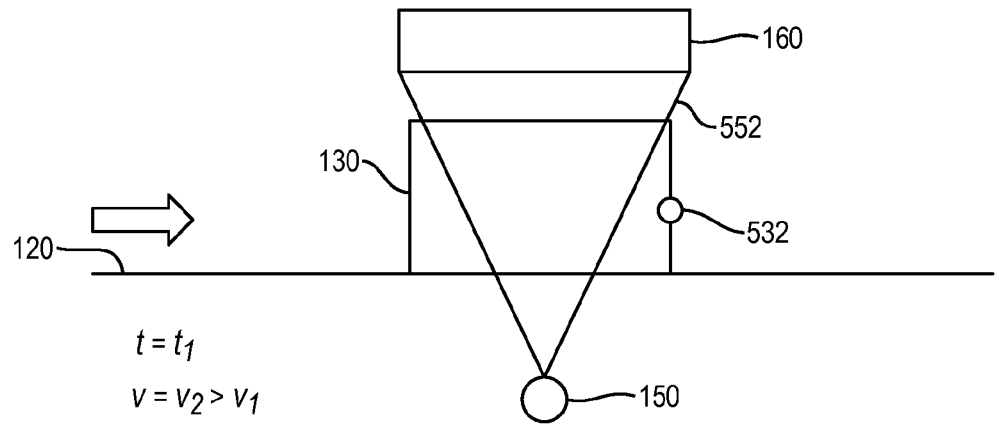

FIGS. 5A-5C illustrate examples of imaging modalities distinguished by the pitch of the imaging system. In this application, the pitch of the imaging system is defined as the advance of an object per X-ray source rotation divided by detector height relative to the advance for which complete geometrical coverage is obtained, where the height of the detector is measured along the coordinate defined by the direction of transport of the object.

FIG. 5A illustrates a side-view of an object 130 being transported past a rotating X-ray source 150 and detector 160. The source 150 and the detector 160 are radially aligned with respect to each other and rotate in unison as mounted to a gantry. The gantry includes a central bore through which the object 130 passes. The illustration in FIG. 5A is a snapshot at an initial time $t_0$ as an arbitrary point 532 on the object 130 has just become illuminated by a conical beam 552 emitted by the X-ray source 150. As the object 130 moves from left to right, the X-ray source 150 and detector 160 rotate about the object 130 as the transport system 120 transports the object 130 through the central bore of the gantry.

In FIG. 5B, the X-ray source 150 and detector 160 have rotated through an angle of 180° at a time $t_1>t_0$. The illustration in FIG. 5B illustrates a snapshot at time $t_1$ in the case where the speed of transport of the object 130 $v_1$ allows complete pi-line coverage to be obtained. In FIG. 5B, the X-ray source 150 and detector 160 have rotated by 180° around the object 130. Because the object 130 is still within the cone of illumination of the beam 552 at a time $t_1$, information is obtained for the full range of angles at the arbitrarily chosen point 532 over the time period from $t_0$ to $t_1$. In the modality illustrated in FIG. 5B, the pitch is approximately equal to 1. At a pitch of about 1 or less, the imaging system is able to obtain 180° of measurement data about the point in the object. Angular coverage of 180° of measurement data satisfies pi-line completeness requirements.

In FIG. 5C, the speed of the object 130 relative to the rotational speed of the X-ray source 150 and the detector 160 is increased with respect to the imaging modality illustrated in FIG. 5B. The imaging modality illustrated in FIG. 5C has a pitch greater than 1. FIG. 5C illustrates an example of an operation that is insufficient for complete pi-line coverage (also referred to herein as incomplete pi-line coverage). Here, the speed of transport of the object 130 $v_2>v_1$ is sufficient to cause the arbitrary point 532 to pass out of the cone of illumination from the X-ray source 150 by the time $t_1$. In other words, information cannot be obtained for a full angular coverage of 180° relative to the scan path for point 532 because the point passes through the illumination cone before the cone can traverse at least 180° about the object 130.

In accordance with various embodiments, imaging devices as taught herein may operate in a first mode and a second mode where the speeds of the transport system relative to a scan path are sufficient and insufficient, respectively, to collect complete pi-line measurement data. In other words in one mode, for example a first mode, a speed at which an object is transported through the emitted beam relative to the speed of rotation of the beam allows establishment of a pi-line through a point in the object. In another mode, for example a second mode, the speed at which the object is transported through the emitted beam relative to the speed of rotation of the beam does not allow establishment of a pi-line through the point in the object. In an exemplary embodiment, the speed of the transport system can be about 15 cm/s in the first mode and about 30 cm/s in the second mode.

Figure 6:
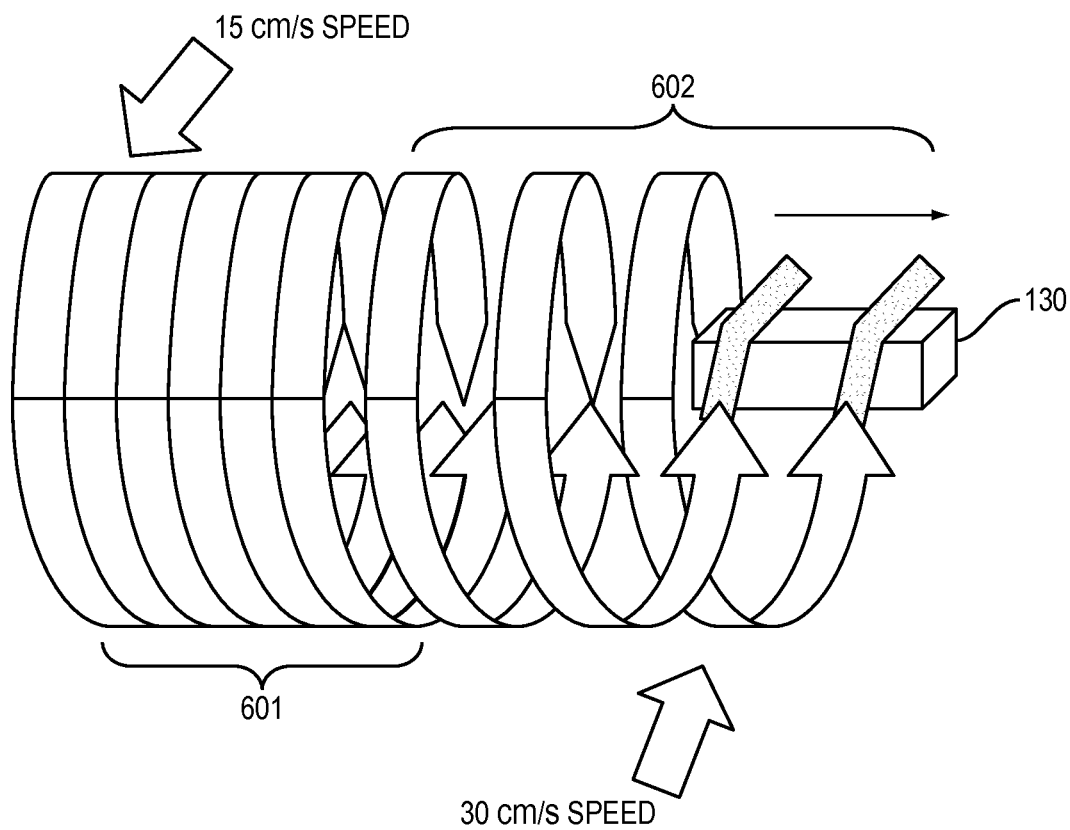
FIG. 6 illustrates changes in scan coverage for different speeds of a transport system, according to embodiments of the present disclosure.

FIG. 6 illustrates in more detail the difference in imaging modalities between the first mode and the second mode. In a first mode 601, the object 130 is transported at a speed of about 15 cm/s. In the first mode 601, neighboring spirals are contiguous or overlapping to indicate that there are no gaps in coverage. In the second mode 602, the object 130 is transported at a speed of about 30 cm/s. In the second mode 602, scan coverage is not contiguous and areas without scan coverage occur between neighboring spirals. The open space indicates that the coverage is incomplete, i.e., measurement data corresponding to each point in the object 130 is not obtained over a full 180 degrees.

Figure 7B:
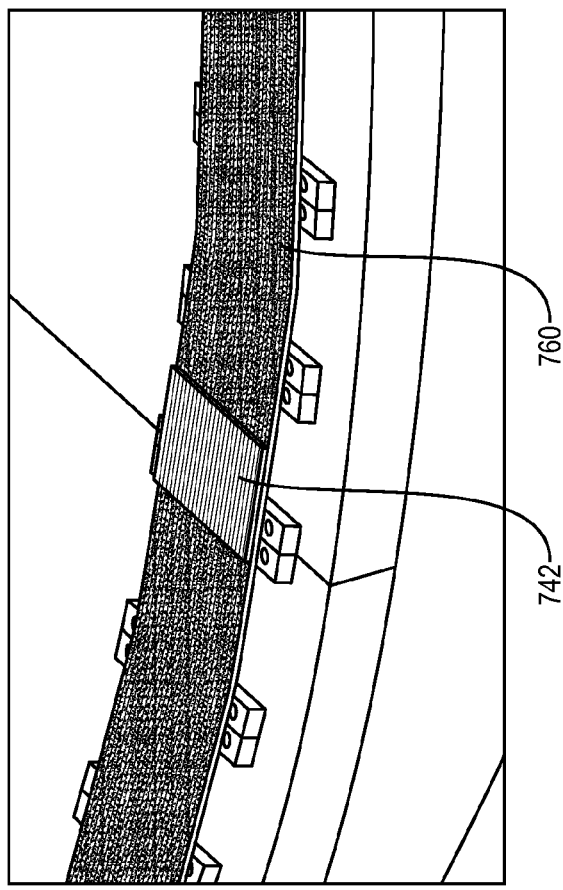
FIGS. 7A and 7B illustrate views of example gantry systems, according to embodiments of the present disclosure.
Figure 7A:
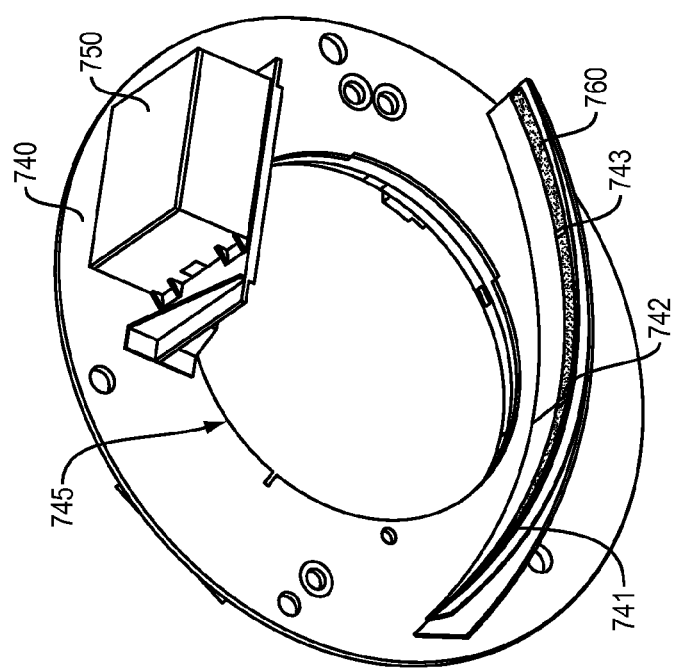

An example rotating gantry according to various embodiments is depicted in FIGS. 7A and 7B. The gantry 740 includes an opening or central bore 745 through which objects may pass in connection with a transport system as discussed above. The X-ray source 750 may be located on the gantry 740, and the detector array 760 may be located substantially opposite the X-ray source across the opening.

In some embodiments, a coating such as a metal foil 741, 742, 743 can be overlaid on one or more elements of the detector array 760. The coated elements 741, 742, 743 may be sensitive to different radiation energy than the exposed elements. With these secondary energy detector elements interpolated within the main detector array 760, embodiments taught herein may be capable of measuring volume properties such as atomic number or elemental composition. The introduction of secondary energy detector elements can leave gaps in the dataset when performing a volumetric data reconstruction for a property that requires low energy radiation such as density. The gaps in the volumetric data may be filled by interpolation of neighboring values, averaging, or by any other suitable method.

Figure 8:
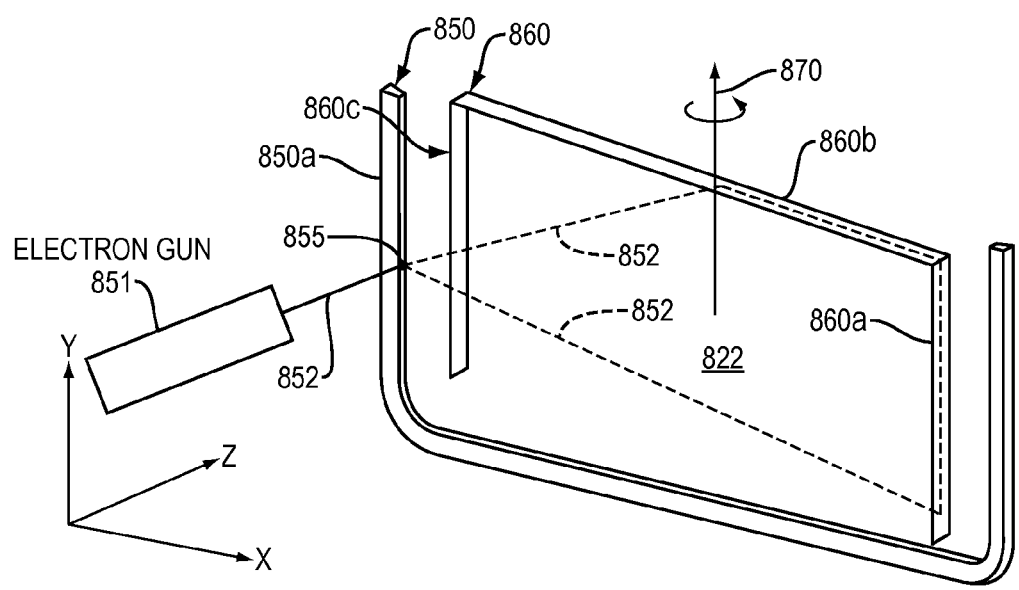
FIG. 8 illustrates an example X-ray source and detector geometry and relationship for systems and devices, according to some embodiments of the present disclosure.

FIG. 8 illustrates an X-ray source target 850 and a detector array 860 geometry and relationship according to some embodiments. In some embodiments, the X-ray source target 850 is activated by a high-energy electron beam 852 from an electron source 851. For example, an e-beam 852 can be directed to impinge on target 850, which responds by emitting X-rays in $4\pi$ directions. Collimators (not shown) may be used to form the emitted radiation into a fan beam, cone beam, pencil beam, or other shaped beam as dictated by application-specific requirements. The shaped beam of radiation enters an examination region 822 through which an object passes. A detector array 860 may be located diametrically opposite to the radiation emission point and can respond to the attenuated beam of radiation. For example, the detectors along arms 860a and 860b of the detector array 860 detect X-rays in the fan beam generated along arm 850a, for example, fan beam 852 emitted by X-ray source location 855. In accordance with various embodiments, the plane defined by the detector array can be rotated by an angle 870 with respect to the plane defined by the X-ray source target 850. Rotation by an angle 870 can help to avoid a situation in which X-rays emitted from the X-ray source target 850 are blocked by an arm of the detector array before passing through the examination region 822. For example, radiation emitted at location 855 will be blocked on the outer surface of detector arm 860c if the rotation angle 870 is zero. By introducing a non-zero rotation angle 870, radiation is free to pass into the examination region 822 before impinging on detector arms 860a and 860b as described above. The electron beam 852 can be steered to control and sweep the X-ray source target 850 including location 855. In example embodiments where the X-ray source target 850 includes multiple targetable elements, the scanning electron beam 852 can be further configured to irradiate some or all of the targetable elements. In some embodiments, a multitude of targetable elements may be disposed at angles along a trajectory of at least 180° about the direction of transport of an object.

The X-ray source target 850 and detector array 860 are suitable for use in the imaging system 100. In this embodiment, the beam of electrons 852 from the electron source 851 is swept across the surface of the X-ray source target 850 to cause emission of X-rays over an angular range of less than 180° or at least 180° about the direction of transport of the object 130. Likewise, the speed of transport of an object relative to the scanning speed of the electron beam to cause emission of X-rays from the X-ray source target 850 is controlled to provide an imaging modality with a pitch approximately equal to 1 or greater than 1.

Figure 9:
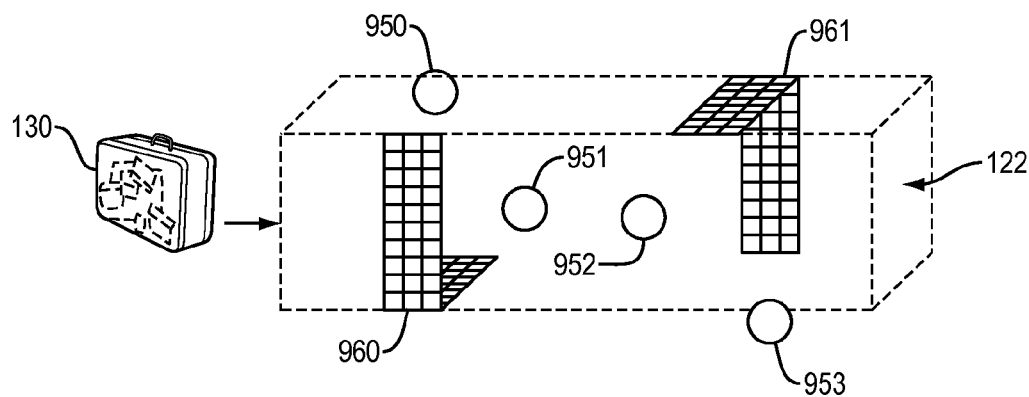
FIG. 9 illustrates an example X-ray source and detector geometry and relationship for systems and devices, according to some embodiments of the present disclosure.

FIG. 9 illustrates an example X-ray source and detector geometry according to some embodiments taught herein. In some embodiments, the X-ray source and detector are both fixed in location and do not rotate. As shown in FIG. 9, a detector array 960 may have multiple segments that form an L-shape or staple shape to cover a greater complement of angles around an object 130. In some exemplary systems, multiple detectors 960, 961 can be included within a single system at different locations along the tunnel 122 traversed by the object 130. An exemplary system using fixed (i.e., non-rotating or moving) X-ray sources and detectors may include multiple X-ray sources 950, 951, 952, 953 that each emit radiation beams toward detectors 960, 961. The X-ray sources 950, 951, 952, 953 can be controlled such that only one X-ray source emits toward a given detector at any point in time so that the received measurement data can be properly associated with the correct X-ray source. Multiple X-ray sources 950, 951, 952, 953 may be skewed such that the range of angles between a given X-ray source and detector array is not duplicated by another X-ray source and detector combination. It will be apparent to one skilled in the art that any number of X-ray sources and detector arrays could be disposed within an imaging system to achieve any total angular coverage dictated by the specifics of the application. In accordance with various embodiments, the sources 950, 951, 952, 953 can be extended targets that emit X-rays when stimulated by a high energy electron beam as described above in relation to FIG. 8. In such embodiments, one or more fixed electron beam sources can be configured to irradiate positions along the extended targets. In some embodiments, each extended target can extend through a range of angles of less than 180°, at least 180°, or more than 180° about the direction of transport of an object.

The X-ray sources 950, 951, 952, 953 and detectors 960, 961 are suitable for use in the imaging system 100. In this embodiment, the X-ray sources 950, 951, 952, 953 are controlled to emit and the detectors 960, 961 are controlled to receive X-rays over a range of angles of less than 180° or at least 180° about the direction of transport of the object 130. Likewise, the speed of transport of an object relative to the speed of the sequence of X-ray emission and detection is controlled to provide an imaging modality with a pitch approximately equal to 1 or greater than 1.

Figure 10:
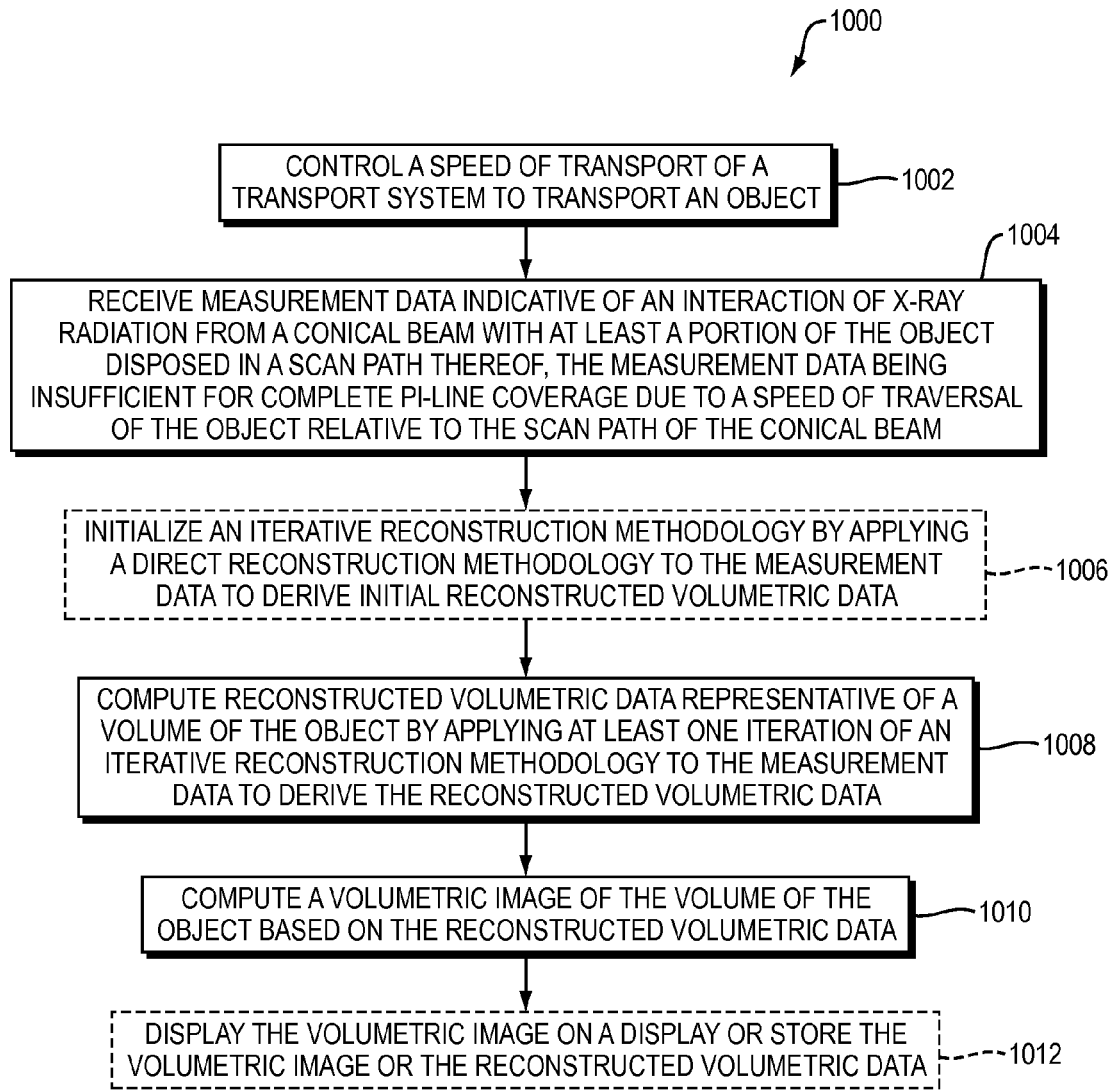
FIG. 10 illustrates a flowchart of an example image reconstruction methodology, according to embodiments of the present disclosure.

FIG. 10 illustrates a flowchart of an image reconstruction of a volume of an object from a cone-beam radiation pattern. In step 1002, the speed of a transport system is controlled to transport an object. The image reconstruction 1000 also includes a step 1004 of receiving measurement data indicative of an interaction of X-ray radiation from a conical beam with at least a portion of an object disposed in a scan path thereof. The measurement data is insufficient for complete pi-line coverage due to a speed of traversal of the object relative to the scan path of the conical beam. In some embodiments, step 1006 may be performed to initialize an iterative reconstruction methodology by applying a direct reconstruction methodology to the measurement data to derive initial reconstructed volumetric data. In some embodiments, a direct reconstruction methodology may be bypassed or not used. The image reconstruction 1000 also includes a step 1008 of computing reconstructed volumetric data representative of a volume of the object by applying at least one iteration of an iterative reconstruction methodology to the measurement data to derive the reconstructed volumetric data. The image reconstruction 1000 also includes a step 1010 of computing a volumetric image of the volume of the object based on the reconstructed volumetric data. In some embodiments, a step 1012 may be performed to display on a display the volumetric image or store the volumetric image or the reconstructed volumetric data.

FIG. 10 is described below in greater detail in relation to FIG. 1. In step 1002, computing device 140 controls the speed of the transport system 120 to transport the object 130. In step 1004, measurement data is received at the computing device 140 from the detector 160. The data from the detector 160 is indicative of an interaction of X-ray radiation from a conical beam of the X-ray source 150 with at least a portion of the object 130. The measurement data is insufficient for complete pi-line coverage due to a speed of traversal of the object 130 via the transport system 120 relative to the scan path of the conical beam.

In some embodiments, a step 1006 is performed. In step 1006, an iterative reconstruction methodology is initialized by the computing device 140 by applying a direct reconstruction methodology to the measurement data to derive initial reconstructed volumetric data.

In step 1008, reconstructed volumetric data representative of a volume of the object 130 is computed by the computing device 140 by applying at least one iteration of an iterative reconstruction methodology to the measurement data to derive the reconstructed volumetric data.

In step 1010, a volumetric image of the volume of the object 130 is computed by the computing device 140 based on the reconstructed volumetric data.

In some embodiments, a step 1012 is performed. In step 1012, the volumetric image is displayed on a display 142 or the volumetric image or reconstructed volumetric data is stored. As will be described in greater detail below, the volumetric image or reconstructed volumetric data can be stored in a memory 1106 or storage 1124.

Figure 11:
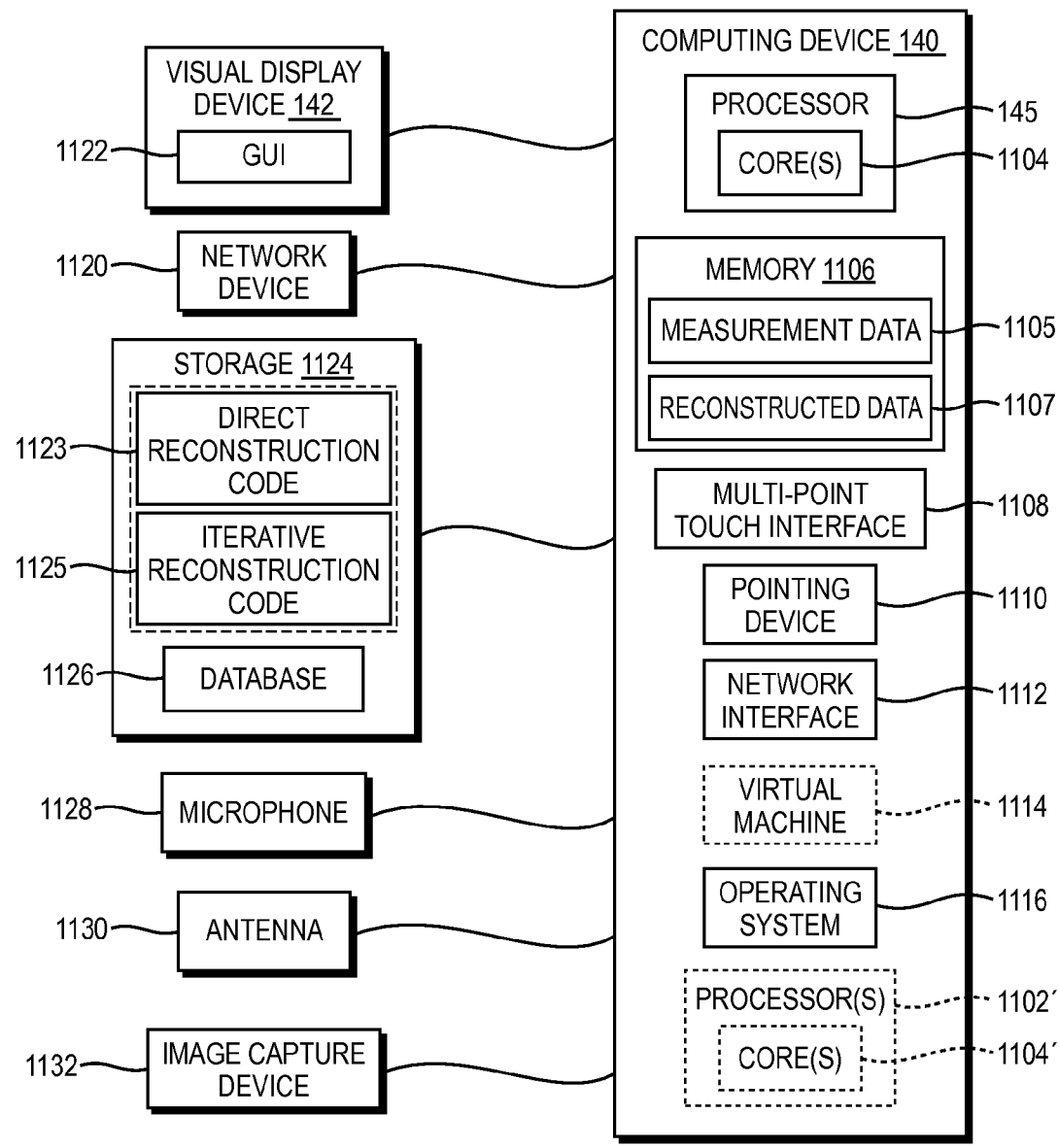
FIG. 11 illustrates an example computing device, according to embodiments of the present disclosure.

FIG. 11 is a block diagram of an exemplary computing device 140 that may be used to implement exemplary embodiments of the image reconstruction methods and systems described herein. Descriptions and elements of the computing device 140 below may be applicable to any computing device described above with reference to previous embodiments. The computing device 140 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 1106 included in the computing device 140 may store computer-readable and computer-executable instructions or software for implementing exemplary embodiments of the imaging system 100. The computing device 140 also includes configurable or programmable processor 145 and associated core(s) 1104 and may include one or more additional configurable or programmable processor(s) 1102' and associated core(s) 1104' (for example, in the case of computer systems having multiple processors or cores), for executing computer-readable and computer-executable instructions or software stored in the memory 1106 and other programs for controlling system hardware. Processor 145 and processor(s) 1102' may each be a single core processor or multiple core (1104 and 1104') processor.

Virtualization may be employed in the computing device 140 so that infrastructure and resources in the computing device may be shared dynamically. A virtual machine 1114 may be provided to handle a process running on multiple processors so that the process appears to be using only one computing resource rather than multiple computing resources. Multiple virtual machines may also be used with one processor.

Memory 1106 may include a computer system memory or random access memory, such as DRAM, SRAM, EDO RAM, and the like. Memory 1106 may include other types of memory as well, or combinations thereof. In some embodiments, the memory 1106 can be used to store measurement data 1105 or reconstructed volumetric data 1107.

A user may interact with the computing device 130 through the visual display device 142, such as a computer monitor, which may display one or more graphical user interfaces 1122, that may be provided in accordance with exemplary embodiments. The computing device 140 may include other I/O devices for receiving input from a user, for example, a keyboard or any suitable multi-point touch interface 1108, a pointing device 1110 (e.g., a mouse), a microphone 1128, or an image capturing device 1132 (e.g., a camera or scanner). The multi-point touch interface 1108 (e.g., keyboard, pin pad, scanner, touch-screen, etc.) and the pointing device 1110 (e.g., mouse, stylus pen, etc.) may be coupled to the visual display device 142. The computing device 140 may include other suitable conventional I/O peripherals.

The computing device 140 may also include one or more storage devices 1124, such as a hard-drive, CD-ROM, or other computer readable media, for storing data and computer-readable instructions or software that implement exemplary embodiments of an imaging system 100. For example, the storage 1124 can store one or more implementations of direct reconstruction executable codes 1123 or iterative reconstruction executable codes 1125 that are further discussed above in connection with FIG. 1. Exemplary storage device 1124 may also store one or more databases for storing any suitable information required to implement exemplary embodiments. For example, exemplary storage device 1124 can store one or more databases 1126 for storing information, such as transport system speed, items scanned, number of alarm triggers, sensor information, system geometry, X-ray source calibration, time since last system maintenance, lifetime usage, or any other information to be used by embodiments of the system 100. The databases may be updated manually or automatically at any suitable time to add, delete, or update one or more data items in the databases.

The computing device 140 can include a network interface 1112 that can be used to transmit or receive data, or communicate with other devices, in any of the example embodiments described herein. Network interface 1112 can be configured to interface via one or more network devices 1120 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing device 140 can include one or more antennas 1130 to facilitate wireless communication (e.g., via the network interface) between the computing device 140 and a network. The network interface 1112 may include a built-in network adapter, network interface card, PCMCIA network card, card bus network adapter, wireless network adapter, USB network adapter, modem or any other device suitable for interfacing the computing device 140 to any type of network capable of communication and performing the operations described herein. Moreover, the computing device 140 may be any computer system, such as a workstation, desktop computer, server, laptop, handheld computer, tablet computer (e.g., the iPad™ tablet computer), mobile computing or communication device (e.g., the iPhone™ communication device), internal corporate devices, or other form of computing or telecommunications device that is capable of communication and that has sufficient processor power and memory capacity to perform the operations described herein.

The computing device 140 may run any operating system 1116, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 1116 may be run in native mode or emulated mode. In an exemplary embodiment, the operating system 1116 may be run on one or more cloud machine instances.

Figure 12:
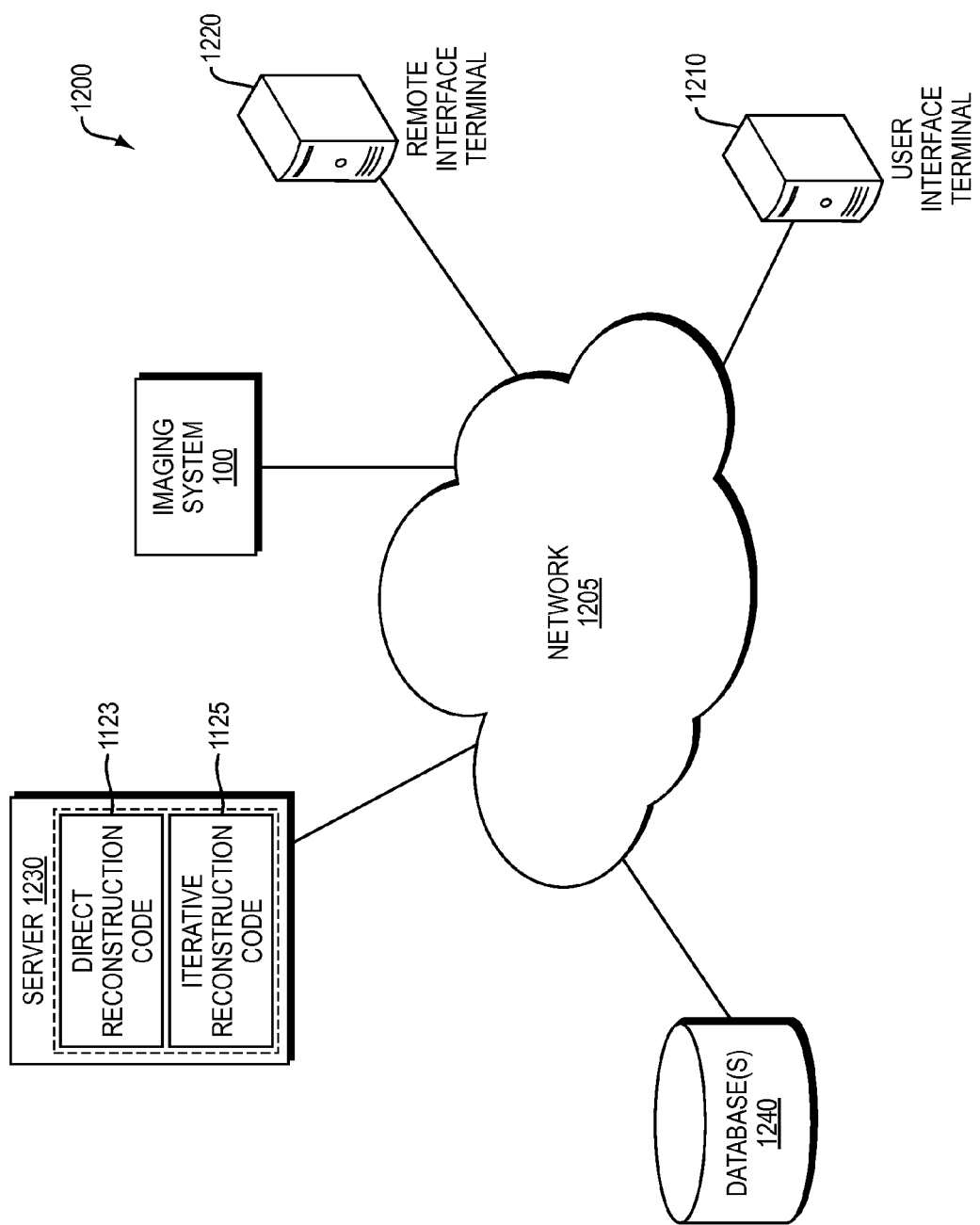
FIG. 12 illustrates an example distributed imaging system, according to embodiments of the present disclosure.

FIG. 12 illustrates a network diagram of a distributed system 1200 for obtaining and reconstructing volumetric imaging data, according to an example embodiment. The distributed system 1200 allows for remote monitoring of the imaging system 100. In this manner, a remote operator, inspector or supervisor may monitor or review objects undergoing examination in real-time. The system 1200 can include a network 1205, multiple interface terminals such as a user interface terminal 1210 or a remote interface terminal 1220, a server 1230, database(s) 1240, and the imaging system 100. Each of the remote and user interface terminals 1210, 1220, server 1230, database(s) 1240, and imaging system 100 is in communication with the network 1205. The following descriptions and elements of the members of the system 1200 or network 1205 including interface terminals 1210, 1220 may be applicable to any computing device described above with reference to previous embodiments.

In an example embodiment, one or more portions of network 1205 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

The interface terminals 1210, 1220 may include, but are not limited to, work stations, computers, general purpose computers, Internet appliances, hand-held devices, wireless devices, portable devices, wearable computers, cellular or mobile phones, portable digital assistants (PDAs), tablets, ultrabooks, netbooks, laptops, desktops, multi-processor systems, microprocessor-based or programmable consumer electronics, network PCs, mini-computers, smartphones, and the like. The interface terminals 1210, 1220 may be part of the system infrastructure and allow computation of a volumetric data reconstruction operation or visualization of the results from said operation. Being part of the system's infrastructure, the interface terminals 1210, 1220 may be installed within the system or they may be installed or operational outside of the system. For example, a remote interface terminal 1220 may be a mobile device that a user can use at a distance from the system to perform computations, visualizations, or other activities. In another example, the interface terminal 1210, 1220 may be installed in an area away from an imaging system to isolate the user from the public or to allow a single user to perform computation or visualization for multiple systems at the same time. The interface terminals 1210, 1220 can include one or more components described in relation to computing device 140 shown in FIG. 11. In some embodiments, the interface terminal 1210, 1220 may be integrated into the imaging system 100.

The interface terminals 1210, 1220 may also include various external or peripheral devices to aid in performing computation or visualization. Examples of peripheral devices include, but are not limited to, monitors, touch-screen monitors, clicking devices (e.g., mouse), input devices (e.g., keyboard), printers, and the like.

Each of the interface terminals 1210, 1220 may connect to network 1205 via a wired or wireless connection. Each of the interface terminals 1210, 1220 may include one or more applications or systems such as, but not limited to, computational models, a graphical user interface, an imaging system control application, a transport system control application, means to trigger an alarm, and the like. In an example embodiment, the interface terminal 1210, 1220 may perform all the functionalities described herein.

In other embodiments, a computation, reconstruction, or visualization code such as a direct reconstruction executable code 1123 or an iterative reconstruction executable code 1125 may be included on interface terminal 1210, 1220 while the server 1230 performs other functionalities described herein. In yet another embodiment, the interface terminal 1210, 1220 may perform some of the functionalities, and server 1230 includes a computation, reconstruction, or visualization code such as a direct reconstruction executable code 1123 or an iterative reconstruction executable code 1125. For example, interface terminal 1210, 1220 may compute reconstructed images to display to a user while server 1230 controls a drive motor to adjust the speed of a transport system 120 in the imaging system 100. The interface terminal 1210, 1220 or server 1230 can perform elements of the methodologies or systems described above with reference to FIG. 1 including, but not limited to, receiving measurement data and computing reconstructions.

Each of the server 1230, and database(s) 1240, is connected to the network 1205 via a wired or wireless connection. Server 1230 includes one or more computers or processors configured to communicate with interface terminal 1210, 1220, or database(s) 1230 via network 1205. Server 1230 hosts one or more applications or websites accessed by interface terminal 1210, 1220 or facilitates access to the content of database(s) 1240.

Database(s) 1240 include one or more storage devices for storing data or instructions (or code) for use by server 1230, or interface terminal 1210, 1220. Database(s) 1240 and server 1230 may be located at one or more geographically distributed locations from each other or from interface terminal 1210, 1220. Alternatively, database(s) 1240 may be included within server 1230.

Figure 13:
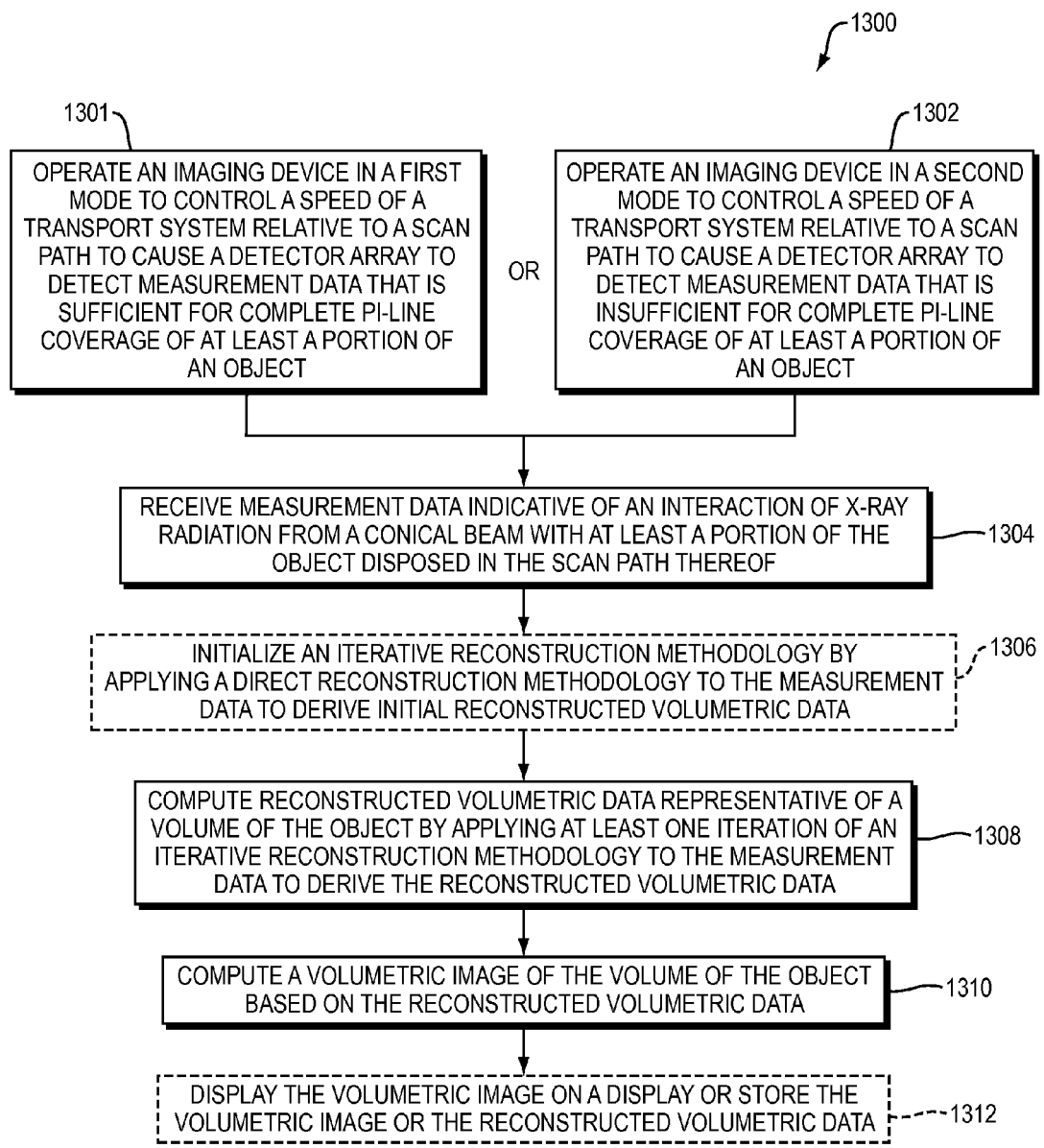
FIG. 13 illustrates a flowchart of an example image reconstruction methodology, according to embodiments of the present disclosure.

FIG. 13 illustrates a flowchart of an image reconstruction of a volume of an object from a cone-beam radiation pattern in a system with two modes of operation. An operator can select the mode of operation in which to operate the imaging system 100 at any time based on a variety of factors. For example, factors may include queue depth of objects to be imaged, security threat level as determined by the Department of Homeland Security or other governmental agencies, or different security protocols along with other factors. One of steps 1301 and 1302 is performed. By selecting step 1301, an imaging device is operated in a first mode to control the speed of a transport system relative to a scan path to cause a detector array to detect measurement data that is sufficient for complete pi-line coverage of at least a portion of an object. The imaging modality in this mode has a pitch less than or equal to 1. By selecting step 1302, an imaging device is operated in a second mode to control the speed of a transport system relative to a scan path to cause a detector array to detect measurement data that is insufficient for complete pi-line coverage of at least a portion of an object. The imaging modality in this mode has a pitch greater than 1.

In step 1304, measurement data indicative of an interaction of X-ray radiation from a conical beam with at least a portion of an object disposed in the scan path thereof is received. In some embodiments, a step 1306 may be performed to initialize an iterative reconstruction methodology by applying a direct reconstruction methodology to the measurement data to derive initial reconstructed volumetric data. In some embodiments, a direct reconstruction methodology may be bypassed or not used. The image reconstruction 1300 also includes a step 1308 of computing reconstructed volumetric data representative of a volume of the object by applying at least one iteration of an iterative reconstruction methodology to the measurement data to derive the reconstructed volumetric data. The image reconstruction 1300 also includes a step 1310 of computing a volumetric image of the volume of the object based on the reconstructed volumetric data. In some embodiments, a step 1312 may be performed to display on a display the volumetric image or store the volumetric image or the reconstructed volumetric data.

FIG. 13 is described below in greater detail in relation to FIG. 1. In step 1301, computing device 140 operates the imaging device 100 in a first mode to control the speed of the transport system 120 to transport the object 130. The speed of the transport system 120 causes the detector 160 to detect measurement data that is sufficient for complete pi-line coverage of at least a portion of the object 130. Alternatively to step 1301, step 1302 may be performed. In step 1302, computing device 140 operates the imaging device 100 in a second mode to control a speed of the transport system 120 to transport the object 130. The speed of the transport system 120 causes the detector 160 to detect measurement data that is insufficient for complete pi-line coverage of at least a portion of the object 130. In step 1304, measurement data is received at the computing device 140 from the detector 160. The data from the detector 160 is indicative of an interaction of X-ray radiation from a conical beam of the X-ray source 150 with at least a portion of the object 130.

In some embodiments, a step 1306 is performed. In step 1306, an iterative reconstruction methodology is initialized by the computing device 140 by applying a direct reconstruction methodology to the measurement data to derive initial reconstructed volumetric data.

In step 1308, reconstructed volumetric data representative of a volume of the object 130 is computed by the computing device 140 by applying at least one iteration of an iterative reconstruction methodology to the measurement data to derive the reconstructed volumetric data.

In step 1310, a volumetric image of the volume of the object 130 is computed by the computing device 140 based on the reconstructed volumetric data.

In some embodiments, a step 1312 is performed. In step 1312, the volumetric image is displayed on a display 142 or the volumetric image or reconstructed volumetric data is stored in a memory 1106 or a storage 1124.

Figure 14:
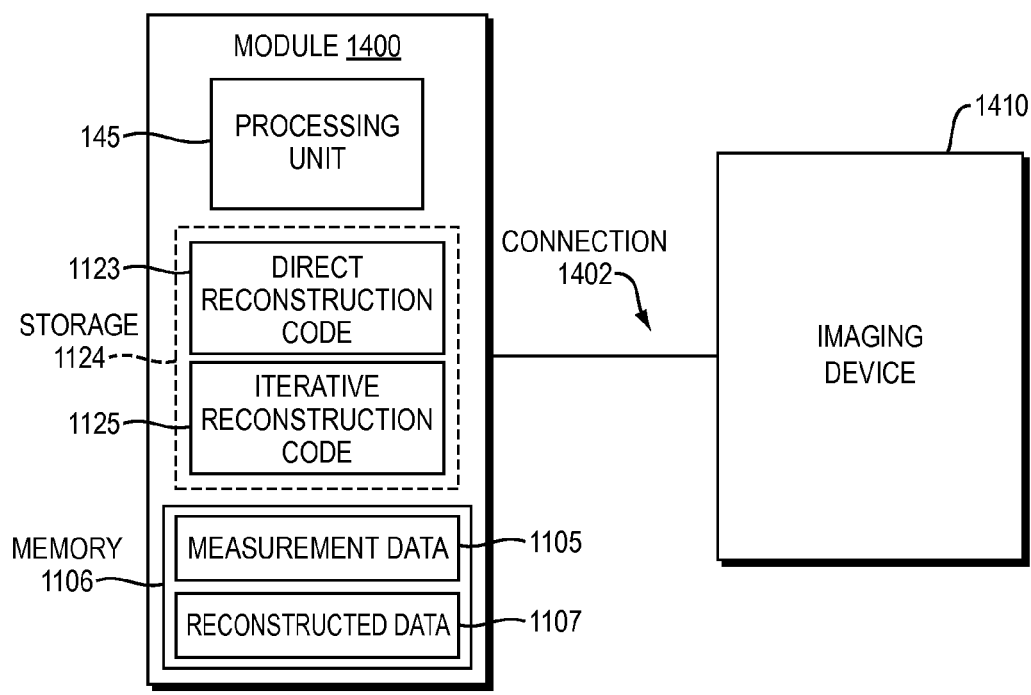
FIG. 14 illustrates an example module, according to embodiments of the present disclosure.

FIG. 14 illustrates an image reconstruction module 1400 having hardware and software components therein. In some embodiments, the image reconstruction module 1400 may be used in combination with an imaging device 1410 to perform aspects of the present disclosure. In some embodiments, the image reconstruction module 1400 can include a processing unit 145, storage 1124, and memory 1106. Elements of the image reconstruction module 1400 such as the processing unit 145, storage 1124, and memory 1106 can operate as described above with reference to, for example, FIGS. 1 and 11. For example, the memory 1106 can hold measurement data 1105 or reconstructed data 1107 while the storage 1124 can be used to store one or more implementations of a direct reconstruction executable code 1123 or an iterative reconstruction executable code 1125. The image reconstruction module 1400 can be operatively coupled to the imaging device 1410 using a wired or wireless connection 1402. Alternatively, the image reconstruction module can be installed within the imaging device 1410. The image reconstruction module 1400 may be used to retrofit an imaging device to provide image reconstruction capabilities as described previously with reference to FIGS. 1 and 10. That is, a system employing the image reconstruction module 1400 and an imaging device can reconstruct volumetric data for an object using measurement data obtained from a detector that is insufficient for complete pi-line coverage due to a speed of traversal of the object relative to a scan path of a conical beam of an X-ray source.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other embodiments, functions and advantages are also within the scope of the invention.

What is claimed is:

1. An imaging device comprising:
a transport system to transport an object;
an X-ray source to emit a conical beam of X-ray radiation at a plurality of points along a trajectory of at least 180° about a direction of transport of the object to irradiate at least a portion of the object;
a detector array to detect measurement data indicative of an interaction of the X-ray radiation with at least the portion of the object, the detector array disposed relative to the X-ray source to detect the measurement data along a scan path about the object; and
a processing unit having a central processing unit programmable to:
operate the imaging device in one of a first mode or a second mode:
the first mode controlling a first speed of the transport system relative to the scan path to cause the detector array to detect measurement data that is sufficient for complete pi-line coverage;
the second mode controlling a second speed of the transport system relative to the scan path to cause the detector array to detect measurement data that is insufficient for complete pi-line coverage, the second speed greater than the first speed; and
compute reconstructed volumetric data representative of a volume of the object in the first mode or the second mode by applying at least one iteration of an iterative reconstruction to the measurement data to derive the reconstructed volumetric data.

2. The imaging device of claim 1 wherein the processing unit is further programmable to derive a volumetric image of the volume of the object based on the reconstructed volumetric data, the volumetric image comprising a three-dimensional model of the volume of the object or a two-dimensional projection of the volume of the object.

3. The imaging device of claim 2, further comprising a display to display the volumetric image.

4. The imaging device of claim 1, wherein the reconstructed volumetric data comprises mass density data or atomic number data or both.

5. The imaging device of claim 1, wherein the X-ray source comprises a conical beam X-ray source coupled to a rotating gantry.

6. The imaging device of claim 5, wherein the rotating gantry is configured to rotate the X-ray source through an angle of at least 180° about the direction of transport of the object.

7. The imaging device of claim 1, wherein the conical beam X-ray source comprises a scanning electron beam configured to irradiate sequentially a plurality of X-ray targets disposed at a plurality of points along a trajectory of at least 180° about the direction of transport of the object.

8. The imaging device of claim 1, wherein the conical beam X-ray source comprises a plurality of fixed electron beams configured to irradiate a plurality of X-ray targets disposed at a plurality of points along a trajectory of at least 180° about the direction of transport of the object.

9. The imaging device of claim 1, wherein the iterative reconstruction comprises at least one of a simultaneous algebraic reconstruction technique (SART), a simultaneous iterative reconstruction technique (SIRT), ordered subset convex technique (OSC), an adaptive statistical iterative reconstruction technique (ASIR), an OS-separable paraboloidal surrogates technique (OS-SPS), an algebraic reconstruction technique (ART), or a Kacsmarz reconstruction technique.

10. The imaging device of claim 1, wherein the processing unit is programmable to:
initialize the iterative reconstruction using an output from a filtered back-projection reconstruction or other direct technique applied to the measurement data; and
perform at least one iteration based on the initialized iterative reconstruction.

11. The imaging device of claim 1, wherein the pi-line through the object connects two different points along the scan path within one pitch in an axial direction, and wherein the measurement data is insufficient for complete pi-line coverage.

12. An imaging system comprising:
a transport system comprising a conveyor, to transport an object into the imaging system;
an X-ray source configured to emit a conical beam of X-ray radiation at a plurality of points along a trajectory of at least 180° around the conveyor on a helical scan path relative to a direction of transport of the object, to irradiate at least a portion of the object, the helical scan path having a pitch greater than one;
a detector array to detect measurement data indicative of an interaction of the X-ray radiation with the portion of the object, the detector array disposed relative to the X-ray source to detect the measurement data along the helical scan path; and
a processing unit having a central processing unit programmable to:
instruct the transport system to transport the object at a speed relative to the helical scan path to cause the detector array to detect measurement data that is insufficient for complete pi-line coverage due to a speed of traversal of the object relative to the helical scan path of the conical beam; and
compute reconstructed volumetric data representative of a volume of the object by applying at least one iteration of an iterative reconstruction to the measurement data to derive the reconstructed volumetric data.

13. The imaging system of claim 12, wherein the processing unit is further programmable to derive a volumetric image of the volume of the object based on the reconstructed volumetric data, the volumetric image comprising a three-dimensional model of the volume of the object or a two-dimensional projection of the volume of the object.

14. The imaging system of claim 13, further comprising a display to display the volumetric image.

15. The imaging system of claim 12, wherein the reconstructed volumetric data comprises mass density data or atomic number data or both.

16. The imaging system of claim 12, wherein the X-ray source comprises a conical beam X-ray source coupled to a rotating gantry.

17. The imaging system of claim 16, wherein the rotating gantry is configured to rotate the X-ray source through an angle of at least 180° about the direction of transport of the object.

18. The imaging system of claim 12, wherein the conical beam X-ray source comprises a scanning electron beam configured to irradiate sequentially a plurality of X-ray targets disposed at a plurality of points along a trajectory of at least 180° about the direction of transport of the object.

19. The imaging system of claim 12, wherein the conical beam X-ray source comprises a plurality of fixed electron beams configured to irradiate a plurality of X-ray targets disposed at a plurality of points along a trajectory of at least 180° about the direction of transport of the object.

20. The imaging system of claim 12, wherein the iterative reconstruction comprises at least one of a simultaneous algebraic reconstruction technique (SART), a simultaneous iterative reconstruction technique (SIRT), ordered subset convex technique (OSC), an adaptive statistical iterative reconstruction technique (ASIR), an OS-separable paraboloidal surrogates technique (OS-SPS), an algebraic reconstruction technique (ART), or a Kacsmarz reconstruction technique.

21. The imaging system of claim 12, wherein the processing unit is programmable to:
initialize the iterative reconstruction using an output from a filtered back-projection reconstruction or other direct technique applied to the measurement data; and
perform at least one iteration based on the initialized iterative reconstruction.

22. The imaging system of claim 12, wherein the pi-line through the object connects two different points along the helical scan path within one pitch in an axial direction, and wherein the measurement data is insufficient for complete pi-line coverage.

23. A method for reconstructing an image of a volume of an object from a cone-beam radiation pattern, comprising:
receiving measurement data indicative of an interaction of X-ray radiation from a conical beam with at least a portion of an object disposed in a scan path thereof, the measurement data being insufficient for complete pi-line coverage due to maintaining a speed of traversal of the object relative to the scan path of the conical beam that prevents complete pi-line coverage;
computing, using at least one processing unit having a central processing unit, reconstructed volumetric data representative of a volume of the object by applying at least one iteration of an iterative reconstruction methodology to the measurement data to derive the reconstructed volumetric data; and
computing, using the at least one processing unit, a volumetric image of the volume of the object based on the reconstructed volumetric data.

24. The method of claim 23, wherein the volumetric image comprises a three-dimensional model of the volume of the object or a two-dimensional projection of the volume of the object.

25. The method of claim 23, further comprising displaying on a display the volumetric image or storing the volumetric image or the reconstructed volumetric data.

26. The method of claim 23, wherein a pi-line through the object connects two different points along the scan path within one pitch in an axial direction, and wherein the measurement data is insufficient for complete pi-line coverage.

27. The method of claim 23, wherein the conical beam emits from a conical X-ray source coupled to a rotating gantry.

28. The method of claim 23, wherein the conical X-ray source comprises a scanning electron beam configured to irradiate sequentially a plurality of X-ray targets disposed at a plurality of points along a trajectory of at least 180° about the direction of transport of the object.

29. The method of claim 23, wherein the conical beam X-ray source comprises a plurality of fixed electron beams configured to irradiate a plurality of X-ray targets disposed at a plurality of points along a trajectory of at least 180° about the direction of transport of the object.

30. The method of claim 23, wherein the iterative reconstruction methodology comprises at least one of a simultaneous algebraic reconstruction technique (SART), a simultaneous iterative reconstruction technique (SIRT), ordered subset convex technique (OSC), an adaptive statistical iterative reconstruction technique (ASIR), an OS-separable paraboloidal surrogates technique (OS-SPS), an algebraic reconstruction technique (ART), or a Kacsmarz reconstruction technique.

31. The method of claim 23, wherein the computing comprises:

initializing the iterative reconstruction methodology using an output from a filtered back-projection reconstruction or other direct technique applied to the measurement data to provide an initialized iterative reconstruction; and performing at least one iteration based on the initialized iterative reconstruction.

32. The method of claim 23, wherein the reconstructed volumetric data comprises mass density data or atomic number data or both.

33. An image reconstruction module for an imaging device, comprising:
a communication interface;
memory to store processor-executable instructions for an iterative reconstruction methodology for computing reconstructed volumetric data representative of a volume of an object; and
a programmable processing unit having a central processing unit, communicatively coupled to the communication interface and the memory, wherein upon execution of the processor-executable instructions, the programmable processing unit operates to:
receive measurement data indicative of an interaction of X-ray radiation from a cone-beam radiation pattern with at least a portion of an object disposed in a scan path thereof, the measurement data being insufficient for complete pi-line coverage due to maintaining a speed of traversal of the object relative to the scan path that prevents complete pi-line coverage;
compute reconstructed volumetric data representative of a volume of the object by applying at least one iteration of an iterative reconstruction methodology to the measurement data to derive the reconstructed volumetric data;
compute a volumetric image of the volume of the object based on the reconstructed volumetric data; and
control the communication interface to transmit, or control the memory so as to store, the volumetric image or the reconstructed volumetric data.

34. The module of claim 33, wherein the volumetric image comprises a three-dimensional model of the volume of the object or a two-dimensional projection of the volume of the object.

35. The module of claim 34, further comprising a display to display the volumetric image.

36. The module of claim 33, wherein the reconstructed volumetric data comprises mass density data or atomic number data or both.

37. The module of claim 33, wherein the iterative reconstruction comprises at least one of a simultaneous algebraic reconstruction technique (SART), a simultaneous iterative reconstruction technique (SIRT), ordered subset convex technique (OSC), an adaptive statistical iterative reconstruction technique (ASIR), an OS-separable paraboloidal surrogates technique (OS-SPS), an algebraic reconstruction technique (ART), or a Kacsmarz reconstruction technique.

38. The module of claim 33, wherein the processing unit is programmable to:
initialize the iterative reconstruction using an output from a filtered back-projection reconstruction or other direct technique applied to the measurement data; and
perform at least one iteration based on the initialized iterative reconstruction.

39. The module of claim 33, wherein the pi-line through the object connects two different points along the scan path within one pitch in an axial direction, and wherein the measurement data is insufficient for complete pi-line coverage.

40. A non-transitory machine readable medium storing instructions executable by a processing device having a central processing unit, wherein execution of the instructions causes the processing device to carry out a method for reconstructing a volume of an object from a cone-beam radiation pattern, the method comprising:
receiving measurement data indicative of an interaction of X-ray radiation from a cone-beam radiation pattern with at least a portion of an object disposed in a scan path thereof, the measurement data being insufficient for complete pi-line coverage due to maintaining a speed of traversal of the object relative to the scan path that prevents complete pi-line coverage;
computing reconstructed volumetric data representative of a volume of the object by applying at least one iteration of an iterative reconstruction methodology to the measurement data to derive the reconstructed volumetric data; and
computing a volumetric image of the volume of the object based on the reconstructed volumetric data.

41. The machine readable medium of claim 40, wherein the volumetric image comprises a three-dimensional model of the volume of the object or a two-dimensional projection of the volume of the object.

42. The machine readable medium of claim 41, wherein the method further comprises displaying the volumetric image on a display.

43. The machine readable medium of claim 40, wherein the reconstructed volumetric data comprises mass density data or atomic number data or both.

44. The machine readable medium of claim 40, wherein the iterative reconstruction comprises at least one of a simultaneous algebraic reconstruction technique (SART), a simultaneous iterative reconstruction technique (SIRT), ordered subset convex technique (OSC), an adaptive statistical iterative reconstruction technique (ASIR), an OS-separable paraboloidal surrogates technique (OS-SPS), an algebraic reconstruction technique (ART), or a Kacsmarz reconstruction technique.

45. The machine readable medium of claim 40, wherein the processing unit is programmable to:
initialize the iterative reconstruction using an output from a filtered back-projection reconstruction or other direct technique applied to the measurement data; and
perform at least one iteration based on the initialized iterative reconstruction.

46. The machine readable medium of claim 40, wherein the pi-line through the object connects two different points along the scan path within one pitch in an axial direction, and wherein the measurement data is insufficient for complete pi-line coverage.

* * * * *